(12) United States Patent
Chander

(10) Patent No.: US 12,350,039 B2
(45) Date of Patent: *Jul. 8, 2025

(54) BLOOD ANALYSIS SYSTEM

(71) Applicant: Bal Chander, Himachal Pradesh (IN)

(72) Inventor: Bal Chander, Himachal Pradesh (IN)

(73) Assignee: Bal Chander, Himachal Pradesh (IN)

( * ) Notice: Subject to any disclaimer, the term of this patent is extended or adjusted under 35 U.S.C. 154(b) by 892 days.

This patent is subject to a terminal disclaimer.

(21) Appl. No.: 17/609,281

(22) PCT Filed: May 8, 2020

(86) PCT No.: PCT/IN2020/050415
§ 371 (c)(1),
(2) Date: Nov. 5, 2021

(87) PCT Pub. No.: WO2020/230153
PCT Pub. Date: Nov. 19, 2020

(65) Prior Publication Data
US 2022/0225903 A1    Jul. 21, 2022

(30) Foreign Application Priority Data
May 10, 2019 (IN) .............................. 201911018848

(51) Int. Cl.
*A61B 5/145*    (2006.01)
*A61B 5/1455*   (2006.01)
(Continued)

(52) U.S. Cl.
CPC ...... *A61B 5/14525* (2013.01); *A61B 5/14546* (2013.01); *A61B 5/14557* (2013.01);
(Continued)

(58) Field of Classification Search
None
See application file for complete search history.

(56) References Cited

U.S. PATENT DOCUMENTS

2007/0289928 A1* 12/2007 Umehara ............ A61M 1/3437
  210/805
2013/0149692 A1*  6/2013 Fender ................. A61M 1/308
  435/2

(Continued)

FOREIGN PATENT DOCUMENTS

EP         3238760 A1    11/2017
WO      2002094351 A2    11/2002
WO      2014008490 A1     1/2014

OTHER PUBLICATIONS

Arroyo-Currás et al., "Real-time measurement of small molecules directly in awake, ambulatory animals," PNAS, vol. 114, No. 4, pp. 645-650 (2017).

(Continued)

*Primary Examiner* — Susan S Su
*Assistant Examiner* — Katherine-Ph Minh Pham
(74) *Attorney, Agent, or Firm* — Kendal M. Sheets

(57) ABSTRACT

A blood analysis system for analysis and correction of blood of a subject includes a centrifugation unit to receive blood of a subject. The centrifugation unit is configured to hold capturing molecules for chemical capture of molecules and/or ions that deactivate at least one of coagulation and complement pathways in the blood and centrifuge to suspend cellular components with a minimal plasma along with the capturing molecules. The blood analysis system includes a correction unit coupled to the centrifugation unit to receive the minimal plasma having the capturing molecules and the cellular components from the centrifugation unit. The correction unit is configured to extract the capturing molecules from the minimal plasma, prior to infusing the minimal plasma having the cellular components along with replaced captured molecules and/or ions back to the subject and discarding the extracted capturing molecules.

20 Claims, 6 Drawing Sheets

(51) Int. Cl.
  *A61M 1/34* (2006.01)
  *A61M 1/36* (2006.01)
(52) U.S. Cl.
  CPC .......... *A61M 1/3618* (2014.02); *A61M 1/362* (2014.02); *A61M 1/3633* (2013.01); *A61M 1/3693* (2013.01); *A61M 1/3472* (2013.01); *A61M 1/3479* (2014.02); *A61M 1/3482* (2014.02); *A61M 1/3496* (2013.01); *A61M 2205/7554* (2013.01); *A61M 2230/20* (2013.01)

(56) References Cited

U.S. PATENT DOCUMENTS

| | | | |
|---|---|---|---|
| 2014/0008301 A1 | 1/2014 | Ostafin et al. | |
| 2017/0065762 A1* | 3/2017 | Larsen | B01D 61/0022 |
| 2017/0252497 A1* | 9/2017 | Nosrati | A61M 1/3413 |
| 2017/0348472 A1* | 12/2017 | Pesenti | A61M 1/3675 |
| 2018/0106778 A1* | 4/2018 | Bainbridge | B01D 21/262 |

OTHER PUBLICATIONS

Couture et al., "Modern surface plasmon resonance for bioanalytics and biophysics," Phys. Chem. Chem. Phys., vol. 15, No. 27, pp. 11190-11216 (2013).
Jost et al., "Magnetic quantitative reverse transcription PCR: A high-throughput method for mRNA extraction and quantitative reverse transcription PCR," BioTechniques, vol. 43, pp. 206-211 (2007).
Jubran, A., "Pulse oximetry," Critical Care, vol. 19, No. 272, pp. 1-7 (2015).
Kraft et al., "In Vivo Dopamine Release and Uptake Impairments in Rats Treated with 3-Nitropropionic Acid," Neuroscience, vol. 161, pp. 940-949 (2009).
Mamkin et al., "Real-Time Continuous Glucose Monitoring in the Clinical Setting: The Good, the Bad, and the Practical," Journal of Diabetes Science and Technology, vol. 2, No. 5, pp. 882-889 (2008).
Pretsch, E., "The new wave of ion-selective electrodes," Anal. Chem., vol. 74, No. 15, pp. 420A-426A (2002).
Sarter et al., "Interpreting Chemical Neurotransmission in Vivo: Techniques, Time Scales, and Theories," ACS Chemical Neuroscience, vol. 6, pp. 8-10 (2015).
Thompson et al., "A Perspective on the Application of Biosensor and Lab-On-A-Chip Technologies to Biomarker Detection in Biological Fluids," Austin Journal of Nanomedicine & Nanotechnology, vol. 2, No. 1, p. 1009 (2014).
Int'l Search Report issued Aug. 12, 2020 in Int'l Application No. PCT/IN2020/050415.
Zhang et al, "In vivo Monitoring of Serotonin in the Striatum of Freely-Moving Rats with One-Minute Temporal Resolution by Online Microdialysis-Capillary High Performance Liquid Chromatography at Elevated Temperature and Pressure," Analytical Chemistry, vol. 85, No. 20, pp. 9889-9897 (2013).
Wassum et al, "Transient Extracellular Glutamate Events in the Basolateral Amygdala Track Reward-Seeking Actions," The Journal of Neuroscience, vol. 32, No. 8, pp. 2734-2746 (2012).

* cited by examiner

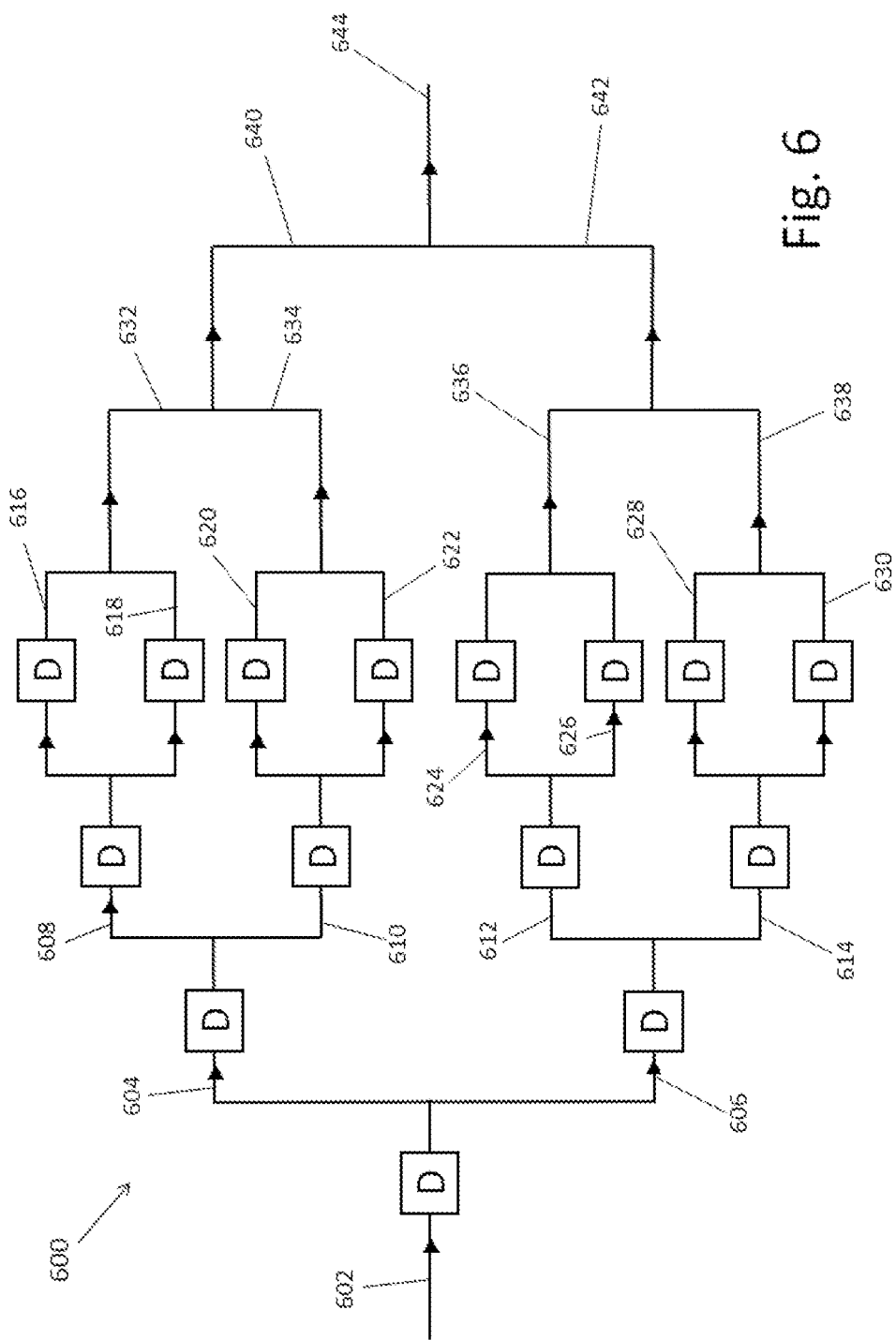

BLOOD ANALYSIS SYSTEM

CROSS-REFERENCE TO RELATED APPLICATIONS

This application is a Section 371 of International Application No. PCT/IN2020/050415, filed May 8, 2020, which was published in the English language on Nov. 19, 2020, under International Publication No. WO 2020/230153 A1, which claims priority under 35 U.S.C. § 119(b) to Indian Application No. 201911018848, filed May 10, 2019, the disclosure of each of which is incorporated herein by reference in its entirety.

TECHNICAL FIELD

The subject matter described herein, in general, relates to physiological and pathological system, and in particular relates to blood analysis and correction system.

BACKGROUND

Body parameters associated with heart and brain activities, and oxygen saturation in mammals can be continuously monitored in real time via ECG machines, EEG machines, BP machines, pulse oxymetry systems, etc. These instruments yield real time information about functionality of vital organs like heart, brain and lungs. However, the underlying molecular/ionic parameters in the blood that have direct bearing on the functions of different organs are not monitored in real time and therefore, we do not know how fluctuations of the blood parameters affect different organs. This assumes importance in critically ill patients. A few modalities are available indeed for instance ion-selective electrodes and implanted devices which can give the reading of only a few molecules in real time (Ref. 1 and Ref. 2 enlisted at the end of the specification).

BRIEF DESCRIPTION OF THE DRAWINGS

The following detailed description references the drawings, wherein:

FIG. 6 illustrates an example of a detection unit, in accordance with the present subject matter.

DETAILED DESCRIPTION

Figure 1:
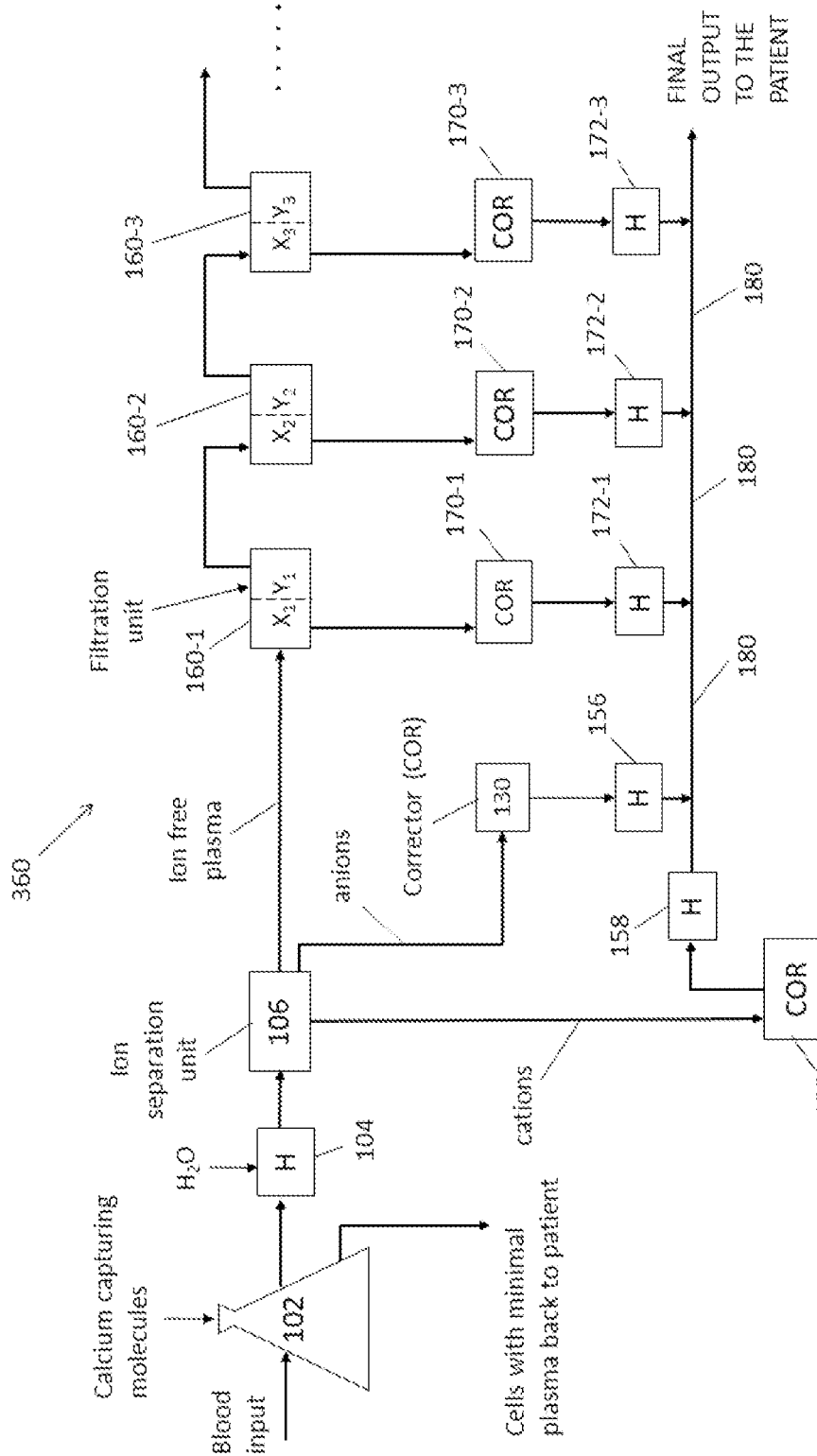
FIG. 1 illustrates an example of a blood analysis system, in accordance with the present subject matter.

At present, if continuous monitoring of all the hormones in the blood is required, one would have to take repeated blood samples and wait for the results to come which, even if a dedicated machine is available, may take at least an hour. Therefore, the patient not only loses blood but the values obtained of the said parameter(s) is/are not in real-time and/or continuous. We end up with values obtained at intervals oblivious to the fact that even hourly measurement does not necessarily mean there must have been no fluctuation of the values during the hour or any interval for that matter. It can be stated that any morbid state or even physiological variations are reflected in blood in the form of variation of levels of molecular and/or ionic entities and that is the reason why measurements of blood parameters make the cornerstone of patient management.

The principle underlying most of the blood, including plasma or serum tests is selective reaction between a molecule and ionic entity and externally added chemical reagents that results in a reaction product. The reaction product can be measured with the help of some kind of spectroscopy and quantified. The quantity of reaction product is related to the molecule/ionic entity under investigation.

Given, the fact that there are thousands of molecules in the blood, selective chemical reaction is a must without any erroneous reaction which might confound the results. However, there are means that can be employed to measure blood parameters without the use of chemical reactions and the foremost among them is Pulse oxymetry. Pulse oxymetry uses the principal of Absorbance. Oxygenated and deoxygenated hemoglobins absorb different lights of wavelength 660 (red) and 940 (infrared). The ratio of red and infrared absorbance is proportional to the oxygenated haemoglobin (blood). It is a non invasive real time measurement of blood oxygen (Ref. 3).

There are other techniques for continuous in vivo real time measurement of molecules like dopamine (Ref. 4), serotonin (Ref. 5), glutamate (Ref. 6) and lactate (Ref. 7) which rely on chemical reaction and therefore have the limitation of measuring only a few entities. Surface based biosensors surface plasmon resonance (SPR) (Ref. 8), quartz crystal microbalances (QCM), field-effect transistors (FET), and microcantilevers have limited practical application when exposed to whole blood since the latter has very high molecular load which leads to non specific adsorption (Ref. 9). Therefore, surface biosensors too have limitation of number of molecules that can be measured in real time. Novel approaches like electrochemical aptamer-based (E-AB) sensors that utilizes conformational changes in response to specific molecules in whole blood to measure the concentration also has the limitation since each aptamer needs to be synthesised for detection of different molecules (Ref. 10).

If one were to use surface based biosensors for the whole blood without unwanted non specific adsorption, the solution would be to reduce the number of type of molecules in the blood as much as possible so that the chances of non specific adsorption are reduced too. The reduction in the type of molecules can be achieved by making use of semi-permeable membranes (one or more than one) with different properties so that only the molecule of interest is the final product which then can be measured utilizing sensors based on surface plasmon resonance (SPR), quartz crystal microbalances (QCM), field-effect transistors (FET), microcantilevers or E-AB with markedly reduced probabilities of nonspecific reactions or interactions.

Alternatively the product of filtration (a few types of molecules) can be measured using any one or combination of different types of spectroscopies or biosensors.

The separation or filtration of types of molecules cannot be achieved in vivo except when only a few types of molecules have to be measured, therefore much more pragmatic solution for measuring more types of molecules in real time would be to carry out the separation or filtration in an extracorporeal system.

Added advantage of extracorporeal system is the controlled correction of level of any or more than one molecule that can be carried out using a novel method of chemical capture without use of drugs and therefore adverse effects. The principle is similar to employed in specific type of real time PCR where mRNA is separated from reaction mixture using oligodeoxythymidylate [oligo(dT)$_{25}$]-coated magnetic particles (Ref. 11).

There are existing medical equipment used for blood purification based on use of semi-permeable membrane with or without adsorption columns listed in the table below The separation or filtration of molecules is routinely carried out in Dialysis where a few types of molecules are filtered out by a semi-permeable membrane. In order to make the filtration as specific as possible and to preserve the ionic balance, the dialysing fluid is constituted such that there is minimal or no disturbance of blood pH or electrolyte balance. The filtered molecules are discarded along with the dialysing fluid.

The key differences between dialysis and the system described in the present disclosure is that:
  i) In latter instead of dialysing fluid, pure water is used
  ii) The target entities are measured in real time preferably using non chemical methods
  iii) Only the target filtered product is captured and discarded along with the pure water
  iv) Rest of the (known and unknown) molecules and ions are retained in the System The purpose of sequential filtration in the system described herein is primarily reduction of types of molecules either in filtrate or retentate which in turn makes it easier to:
  i) detect and quantify a given molecule or molecules with more precision.
  ii) Design capturing molecules with reduced probability of non specific reactions Blood is composed of cellular (red and white blood cells) and acellular (molecular and ionic) components, hereinafter referred to as detectables. If one were to measure all the molecules (excluding ions for the time being) using conventional means, it would take unacceptable amount of blood from the patient considering the fact that there are approximately 30,000 native molecules at any point of time circulating in the blood not to mention drugs with metabolites and microorganism toxins in different clinical situations.

To measure the concentration of detectables in real-time over hours/days or even longer periods of time would be invaluable to not only understand the normal mammalian including human physiology but more importantly changes in different morbid states. Such understanding is vital in order to completely understand pre-mortem changes and the only way to understand the dynamics between thousands of entities present in the blood and indirectly between tissue/organs.

The subject matter described herein relates to blood analysis systems for analysis of blood for various purposes including, but not limited to, medical diagnostics and patient management. The blood analysis system is designed with the view of gaining complete understanding of the molecular basis of physiological and pathological states of mammals as reflected in blood and the use of the attained knowledge to treat disease conditions and/or promote health. The blood analysis systems of the present subject matter are designed for real-time and continuous assessment and manipulation of the levels of all molecules and ionic entities in blood. The blood analysis system of the present subject matter may be referred to as an extracorporeal system, capable of accurate measurement of all molecules and ionic entities without the use of any chemical reaction.

The blood analysis system of the present subject matter is designed to reduce highly complex mixture of molecules in blood to multiple channels each ideally containing only one type of molecule via sequential combination of filtration units with first one filtering out everything but the cells and second one filtering out all molecules except the molecules with parameters within defined range and so on till the last unit which ideally carries only single type of molecule. The blood analysis system of the present subject matter can be used to evaluate all the entities in blood however it can also be contracted to target select group of molecules or just ionic entities.

The blood analysis system of the present subject matter is capable of correction (addition or extraction) of any molecular/ionic level in blood with the use of highly selective chemical reactions and/or adsorption surfaces before returning the blood back into the body. Since selective chemical reaction will occur in the blood analysis system and blood would be returned to the body without any undesirable alterations, the adverse effects of treatment/intervention are minimal or none in comparison to the conventional methods of diagnostics and treatment for many if not most diseases.

The isolation of individual molecular/ionic entities or their separation into small groups in the blood analysis system is done with the sequential use of semi-permeable membranes and electromagnetic forces with or without centrifugation. The semi-permeable membranes separate the given entities based on their molecular size while the electromagnetic forces separate them based on their charge/dipole moment. At every level of separation there are concentration and detection units which make use of electromagnetic waves or electromagnetic fields or voltage difference possibly but not exclusively the form of selective electrodes for detecting and measuring the levels of entities.

Extraction of undesired molecules/ions from a mixture of molecules/ions, when required, is done with the use of specific chemical reaction of the molecule/ion of interest with a pre-specified amount of a reactant of large molecular size or magnetized molecule of any size or both preferably tethered to a catalyst. The product of the reaction is then filtered out within the blood analysis system and the remaining blood components are returned to the body. This method of "chemical capture" is entirely extracorporeal precluding the use of any 'drug' and thereby eliminating the possibility of attendant adverse effects. The chemical capture method of similar nature is employed in specific type of real time PCR where mRNA is separated from reaction mixture using oligodeoxythymidylate [oligo(dT)$_{25}$]-coated magnetic particles (Ref. 11).

In an example implementation, the blood analysis system uses the concept of chemical capture to extract calcium to prevent coagulation within the blood analysis system, thereby eliminating the need for anticoagulants, like heparin. The blood analysis system also makes feasible the selective infusion and capture of drugs at different sites of the body. By the use of this technique, a drug may be infused intra-arterially at the site of intended action with prompt removal of the said drug or its metabolites from the venous end in order to limit the adverse effect of the drug and allowing higher doses to be available at the site of action.

Definitions

All: The word is to be interpreted either in usual sense or it might imply a known fraction with or without other undesirable entities under given set of conditions.

Water: Ultrapure water containing only water molecules or water plus known concentration of molecules and/or ions if latter is necessary for the structural and/or functional stability of the any molecule and/or cells.

Prepared blood/plasma: Suitably diluted blood/plasma so as to reduce the viscosity in such a way that desired flow is achieved facilitating maximum filtration or separation of detectable.

Solution: Blood/Plasma/plasma minus one type of molecule/plasma minus more than one type of molecule.

Channel: Conduit made up of inert material with controlled gating mechanism and flow rate pumps capable of either facilitating or stopping the flow of solution.

Semi-permeable membrane (SPM): A charged/uncharged membrane with selective pore size allowing passage of specific molecules or group of molecules with specific properties, such as molecular weight (MW), shape and dipole moment (DP), and charge, from an area of high concentration to an area of low or zero concentration. Configuration/design of SPM may vary from unit to unit depending upon the isolation of detectable(s).

Cell: Component consisting of two areas/chambers C1 and C2 divided by an SPM. Both areas/chambers C1 and C2 in a cell have respective inlets and outlets for solution, water, detectable/s, filtrate and backwash. All the cells are accompanied by a concentration unit, a detection unit, a correction unit and a holding unit. However some or all of these can be ignored and product (both retained and filtered) of one cell can be directed into the input of second unit directly, depending on the logistics.

Unit: A unit may be a cell, a concentration unit, a holding unit, a detection unit and a correction unit. All inlets and outlets of a unit have separate gates, flow rate pumps, and pressure gauges.

Filtrate: Molecules that have filtered through the SPM from a rea/chamber C1 to area/chamber C2 and suspended in water.

Isotonic saline (IS): 0.9% NaCl with physiological pH.

Concentration unit: Unit composed of components to pump out precise amount of water and ions from a given solution. Inlets and outlet of a concentration unit have separate gates, flow rate pumps, and pressure gauges.

Detectable: Entity/entities (cell/s/molecule/s/ion/s) to be detected using a single or combination of detection unit.

Detection unit: Component having source(s) producing and detecting electromagnetic wave(s) and/or field(s) of varying energies and vectors, such that the interaction with detectable(s) does not result in disruption of any kind of interatomic or intramolecular bond. The changes in electromagnetic wave(s) and/or field(s) is directly proportional to the concentration of the detectable. The detection unit is automated and can be programmed to detect quantitative deviation from any set limit. Furthermore for any given entity the detection unit can automatically work in coordination with the correction unit.

Flow rate pumps: Pump meant to ensure a precise rate of flow incorporated at every inlet and outlet throughout a unit and sequential combination of units/cells ensuring the desired flow rate. Flow rate pumps can also be programmed to ensure optimal flow in the entire System such that no part of the system works without coordination with the other parts.

Holding Unit: Area where, if necessary, concentrated detectable is held for a period of time in order to ensure synchronized reconstitution of blood/plasma/serum. Inlets and outlets of a holding unit have separate gates, flow rate pumps, and pressure gauges. Holding units can also be programmed to ensure optimal flow in the entire System such that no part of the system works without coordination with the other parts.

Correction Unit: Component of semi-permeable membrane which can either extract or introduce any detectable using highly selective chemical reaction to capture and remove one or more than one type of molecule. Correction units can also be programmed to ensure optimal flow in the entire System such that no part of the system works without coordination with the other parts. Detection and correction of any entity/entities can be programmed for automated execution.

Capturing molecule: Synthetic molecule (charged/uncharged/magnetized) with tethered and/or magnetized catalyst with extremely high specificity and sensitivity, such that a capturing molecule shall bind only one type of ion/molecule so that the said ion/molecule is 'captured' and therefore rendered unfunctional. The capturing molecule typically shall be far larger than the ion/molecule such that only the uncaptured ions/molecules in a given mixture shall be able to pass through the SPM or SPM coupled with centrifugation, whereas the capturing molecule with or without captured entity shall not be able to pass through. The amount of capturing molecules can be calculated precisely since the preceding detection unit measures the concentration of entity/entities. Therefore, a precise amount of entity/entities of interest can be manipulated.

Collecting channel: Channel into which filtrate of all outlets empty after detection, measurements, and, if necessary, corrections. Collecting channel can also be programmed to ensure optimal flow in the entire System such that no part of the system works without coordination with the other parts.

Unit control: Computer-readable instructions controlling the functioning of gates, flow rate pumps, and pressure gauges of all inlets and outlets of a unit, such that there is perfect coordination and continuous flow of solution/detectables.

Cell control: Computer-readable instructions controlling the functioning of gates, flow rate pumps, and pressure gauges of all inlets and outlets of a cell, such that there is perfect coordination and continuous flow of solution/detectables.

Central Control: Computer-readable instructions controlling the functioning of gates, flow rate pumps, and pressure gauges of all inlets and outlets of units, cells, and collecting channels, such that there is perfect coordination and continuous flow all detectable and final reconstitution of blood.

The blood analysis system of the present subject matter is a closed loop extracorporeal system configured to detect and measure in real-time all molecular, ionic and cellular entities in blood without using any chemical reaction or make any alterations to molecular structure unless desired. The system is also configured to extract precise amount of one or more than one ionic/molecular entity/entities without using any 'drug'.

The blood analysis system of the present subject matter is configured to perform the following procedure:
  i) draw the blood from a human/animal and direct it into the blood analysis system;
  ii) separate all cellular, molecular and ionic entities or entities with a particular range of properties using centrifugation and/or sequence of filtration units;
  iii) direct each of the filtered entities to its designated channel;

iv) detect and measure the concentration of each entity using non chemical reaction methods that neither disrupts any native intramolecular bond nor forms any;

v) manipulate the levels of any given ionic or molecular entity/entities using unique concept of chemical capture; and vi) reconstitute the blood and infuse back to the human/animal.

With the blood analysis system of the present subject matter, particularly using a sequence of filtration units in the blood analysis system, it is possible to extract any given detectable from blood. The filtration units composed of semi-permeable membranes may allow only entities with size equal or less than a defined molecular weight cut-off.

Once extracted, a single detectable or a mixture of different molecules (solute) in a suitable solvent (water) can be measured by using electromagnetic waves (EMV) or field (EMF) or voltage V of different suitable values/vectors or any other method not preferably but not essentially involving irreversible chemical reaction.

These and other advantages of the present subject matter would be described in a greater detail in conjunction with the FIGS. 1-6 in the following description.

It should be noted that the description merely illustrates the principles of the present subject matter. It will thus be appreciated that those skilled in the art will be able to devise various arrangements that, although not explicitly described herein, embody the principles of the present subject matter and are included within its scope. Furthermore, all examples recited herein are intended only to aid the reader in understanding the principles of the present subject matter. Moreover, all statements herein reciting principles, aspects and implementations of the present subject matter, as well as specific examples thereof, are intended to encompass equivalents thereof.

FIG. 1 illustrates an example of a blood analysis system 360, in accordance with the present subject matter. As shown in FIG. 1, whole blood from a subject, e.g., a human or an animal, along with capturing molecules for calcium are added and centrifuged in a centrifugation unit 102. As a result of centrifugation, all cellular components are suspended in minimal plasma. The suspended cellular components may subsequently be suspended in an isotonic saline if necessary with oxygen and glucose at low temperature. The suspended cellular components may immediately be infused back to the subject, or platelets may be separated using an SPM, passed through a channel, and counted by a detection unit (not shown in FIG. 1). Further, granulocytes and RBCs may be separated using ultracentrifugation, directed to two different channels, and detected/counted by suitable detection units (not shown in FIG. 1). Further, WBCs+RBCs+platelets may be passed through a channel, such that there are no shadow areas and detection units (Not shown in FIG. 1) may detect the type of cells by signature scattering of suitable wavelengths.

The plasma from the centrifugation unit 102 is passed into a holding unit 104, where the plasma may be diluted with water, if necessary, to adjust viscosity such that suitable flow is achieved facilitating maximum filtration at subsequent stages of the blood analysis system 360.

From the holding unit 104, the plasma is passed to an ion separation unit 106, where anions and cations from the plasma are separated using EMF. The anions and the cations may be separated or isolated using the ion separation unit 106 in either order, i.e., the anions before the cations, or the cations before the anions.

Figure 2:
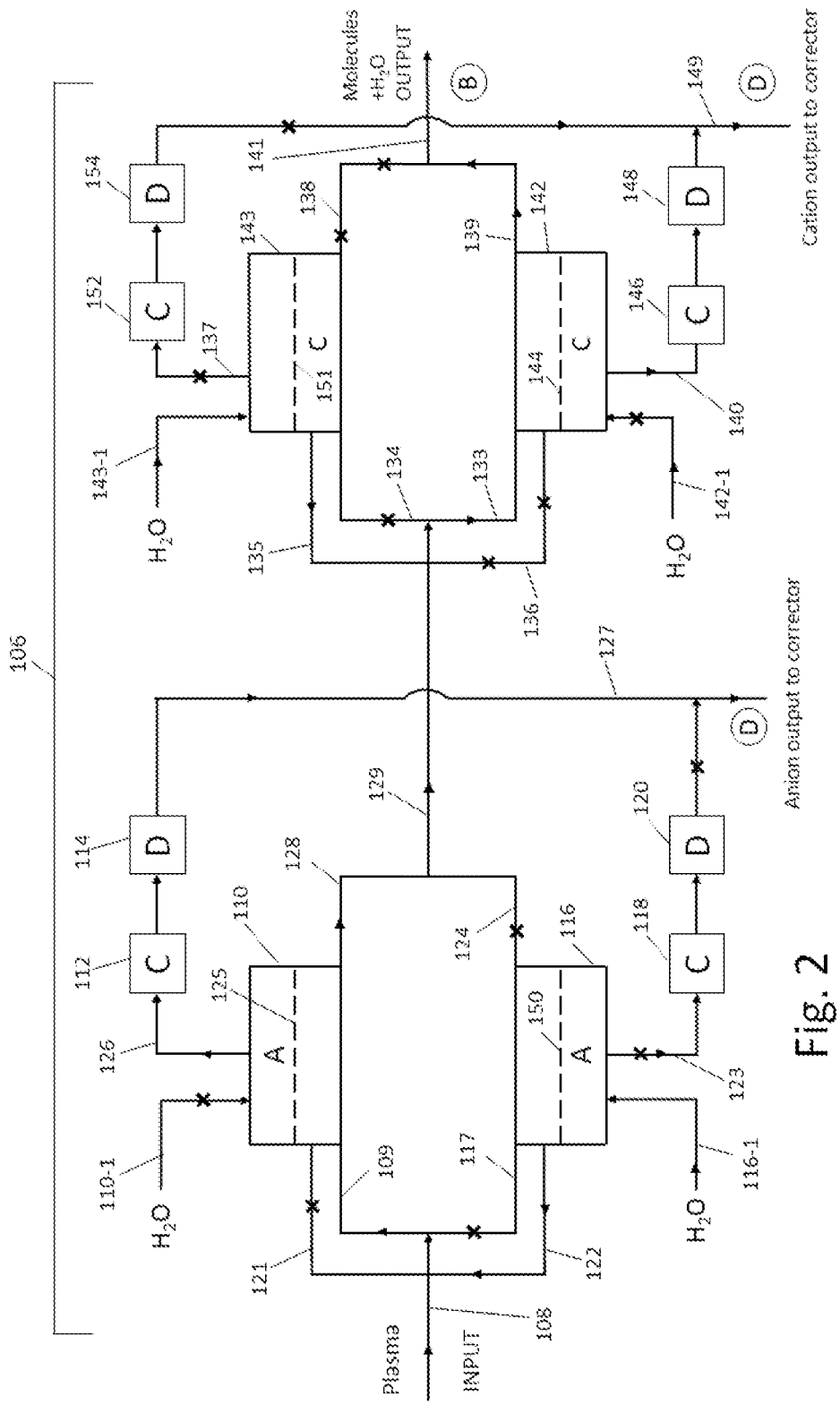
FIG. 2 illustrates an example of an ion separation unit, in accordance with the present subject matter.

Configuration of the Ion Separation Unit 106:

FIG. 2 illustrates an example of an ion separation unit 106, in accordance with the present subject matter. As shown in FIG. 2, the plasma from the holding unit 104 is passed through channel 108 towards channel 109 and then to a cell 110. For said flow of plasma to happen, channels 117, 121, 123 and 124 and 110-1 are kept closed via a respective valve, (every entry/exit of channel/cell has a valve) and water is passed to cell 116 via channel 116-1 to declog SPM 150. The declogged matter is passed to channel 122 which in turn empties into channel 108. The cell 110 has an SPM 125 which allows only anions to pass through. The filtered anions (the filtrate) from the cell 110 are passed through channel 126 to a concentration unit 112 and a detection unit 114, and the remaining plasma (anion-free plasma) from the cell 110 is passed via channels 128 and 129 to a further unit for separation of cations, as explained later in description. The configuration and operation of the concentration unit 112 and the detection unit 114 are described later with reference to FIG. 5 and FIG. 6, respectively. The reconstituted anions from the detection unit 114 are passed via channel 127 to a correction unit 130, as shown in FIG. 1. The configuration and operation of the correction unit 130 are described later with reference to FIG. 3. After necessary correction of anions, they are held in a holding unit 156 which in turn empties into a collecting channel 180 as shown in FIG. 1.

Further, the plasma (anion-free plasma) from channel 129 is passed towards channel 133 and then to a cell 142. For said flow of plasma to happen, channels 134, 136, 137 and 138 and 142-1 are kept closed, and water is passed to cell 143 via channel 143-1 to declog SPM 151. The declogged matter is passed to channel 135 which in turn empties into channel 129. The cell 142 has an SPM 144 which allows only cations to pass through. The cations (the filtrate) from the cell 142 are passed through channel 140 to a concentration unit 146 and a detection unit 148, and the remaining plasma (anion- and cation-free plasma) from the cell 142 is passed via channels 139 and 141 to a filtration unit, as explained later in description. The configuration and operation of the concentration unit 146 and the detection unit 148 are described later with reference to FIG. 5 and FIG. 6, respectively. The reconstituted cations from the detection unit 148 are passed via channel 149 to a correction unit 132, as shown in FIG. 1. The configuration and operation of the correction unit 132 are described later with reference to FIG. 3. After necessary correction of cations, they are held in a holding unit 158 which in turn empties into the collecting channel 180.

After a while, depending on the properties of SPM and the molecular load, the SPM may get clogged. Therefore, it is essential to declog the SPM. Since one of the mandates of the blood analysis system 360 is to have a continuous real-time measurements and corrections of different entities, declogging mechanism while maintaining continuous flow is of paramount importance.

The solution offered is in the form of two parallel identical units such that while one of them if filtering and producing detectable, the other one is getting declogged. This aspect is depicted in FIG. 2, where while the unit 110 is filtering the anions the unit 116 is getting declogged. Each of the units 110 and 116 has a respective SPM 125 and 150, which can allow only anions to pass through. For using the cell 110 for filtering anions and declogging the cell 116, the channels 117, 121, 123, and 124 and 110-1 are kept closed, the channels 109, 122, 126, 128 are kept open, and water is passed through the cell 116 via channel 116-1 to declog SPM 150. The declogged matter is passed to channel 122 which in turn empties into channel 108. Alternately, for using the cell 116 for filtering anions and declogging the cell 110, the channels 117, 121, 123, and 124 and 110-1 are kept open, the channels 109, 122, 126, 128 and 116-1 are kept closed, and water is passed through the cell 110 via channel 110-1. The declogged matter is passed to channel 121 which in turn empties into channel 108. Like for the cell 110, the channel 123 from the cell 116 is connected to a concentration unit 118 and a detection unit 120. The configuration and operation of the concentration unit 118 and the detection unit 120 are described later with reference to FIG. 5 and FIG. 6, respectively. The reconstituted anions from the detection unit 120 are passed via channel 127 to the correction unit 130, as shown in FIG. 1.

Similarly, as depicted in FIG. 2, while the unit 142 is filtering the cations the unit 143 is getting declogged. Each of the units 142 and 143 has a respective SPM 144 and 151, which can allow only cations to pass through. For using the cell 142 for filtering cations and declogging the cell 143, the channels 134, 136, 137, and 138 and 142-1 are kept closed, the channels 133, 135, 139, 140 and 143-1 are kept open, and water is passed through the cell 143 via channel 143-1. The declogged matter is passed to channel 135 which in turn empties into channel 129 Alternately, for using the cell 143 for filtering cations and declogging the cell 142, the channels 134, 136, 137, and 138 and 142-1 are kept open, the channels 133, 135, 139, 140 and 143-1 are kept closed, and water is passed through the cell 142 via channel 142-1. The declogged matter is passed to channel 136 which empties into channel 129. Like for the cell 142, the channel 137 from the cell 143 is connected to a concentration unit 152 and a detection unit 154. The configuration and operation of the concentration unit 152 and the detection unit 154 are described later with reference to FIG. 5 and FIG. 6, respectively. The reconstituted cations from the detection unit 154 are passed via channel 149 to the correction unit 132, as shown in FIG. 1.

Returning to FIG. 1, suitably diluted ion-free plasma from channel 141 of the ion separation unit 106 is then passed through a first filtration unit 160-1 to filter out a first specific type of molecules X1 from the ion-free plasma. The configuration and operation of a filtration unit is described later in the description with reference to FIG. 4. The first specific type of molecules X1, filtered out from the first filtration unit 160-1, suspended in water after concentration and detection are directed to a correction unit 170-1 in order to either pump in extra molecules of the first specific type if the levels are low or extract out the exact amount of molecules of the first specific type if the levels are high. After necessary correction, the first specific type of molecules X1 are held in a holding unit 172-1 which in turn empties into the collecting channel 180.

The plasma with molecules Y1 (filtrate Y1 shown in FIG. 1) from the first filtration unit 160-1, suspended in water after concentration and detection are directed to a second filtration unit 160-2 to filter out a second specific type of molecules X2. The second specific type of molecules X2, filtered out from the second filtration unit 160-2, suspended in water after concentration and detection are directed to a correction unit 170-2 in order to either pump in extra molecules of the second specific type if the levels are low or extract out the exact amount of molecules of the second specific type if the levels are high. After necessary correction, the second specific type of molecules X2 are held in a holding unit 172-2 which in turn empties into the collecting channel 180.

The plasma with molecules Y2 (filtrate Y2 shown in FIG. 1) from the second filtration unit 160-2, suspended in water after concentration and detection are directed to a third filtration unit 160-3 to filter out a third specific type of molecules X3. The third specific type of molecules X3, filtered out from the third filtration unit 160-3, suspended in water after concentration and detection are directed to a correction unit 170-3 in order to either pump in extra molecules of the third specific type if the levels are low or extract out the exact amount of molecules of the third specific type if the levels are high. After necessary correction, the third specific type of molecules X3 are held in a holding unit 172-3 which in turn empties into the collecting channel 180.

The plasma with molecules Y3 (filtrate Y3 shown in FIG. 1) from the second filtration unit 160-3, suspended in water after concentration and detection may either be directed to another filtration unit (not shown) to filter out a further specific type of molecules from the plasma with molecules Y3, or directed to the collection channel 180.

In an example implementation, the blood analysis system 360 may include N number of filtration units to filter out N number of specific types of molecules from the ion-free plasma. One filtration unit is ideally configured to filter out one specific type of molecules but more than one type of molecules with given electrochemical and physical properties can also be filtered out provided accurate detection system to measure the levels of same is in place. Each of the filtration units of the blood analysis system 360 may be configured to operate in the same manner. The configuration and operation of a filtration unit is described later in the description with reference to FIG. 4.

Configuration of the Correction Unit 130/132/170-1/170-2/170-3:

Usually it is done by making use of adsorption. However, there are limitation of adsorption as for each molecule or ion to be removed one has to fabricate specific adsorbing surface. So, for instance a patient of septicemia requiring removal of bacterial products and proinflammatory cytokines, different adsorption surfaces have to be fabricated. In addition, the adsorption cannot be controlled so as to remove precise amount of said entity/entities. To continue with the example of septicemia it may not be advisable to remove all the proinflammatory cytokines.

The proposed principle for selective removal of molecular or ionic entities is very specific chemical reaction, in which the reaction product in aqueous medium will be retained in the unit (i.e., reaction products do not pass through the SPM of the unit) owing to the size and/or charge, whereas rest of the molecules and ionic entities can pass through the SPM. The amount of the entity to be removed can be controlled as the concentration of the entities is already known.

In order to remove any molecular/ionic entity shall require engineering of a capturing molecule which shall bind or capture only one type of entity. Since such chemical reaction shall require a catalyst, the catalyst itself can be incorporated or tethered onto the capturing molecule thereby making separate removal of catalyst from the circulation unnecessary. Alternatively, the catalyst itself can be separate but magnetized or charged to facilitate the subsequent removal via application of suitable magnetic field or SPM.

At present elevated levels of Sodium, or Potassium, or Calcium, etc., require therapeutic maneuvers demanding extreme care including management of adverse effects.

Chemical Capture can remove excess amount of any entity without any drug. It can be any number of types of ionic/molecular entities that are logistically possible to handle. The definition of capturing molecules is included under the Definitions mentioned above.

Figure 3:
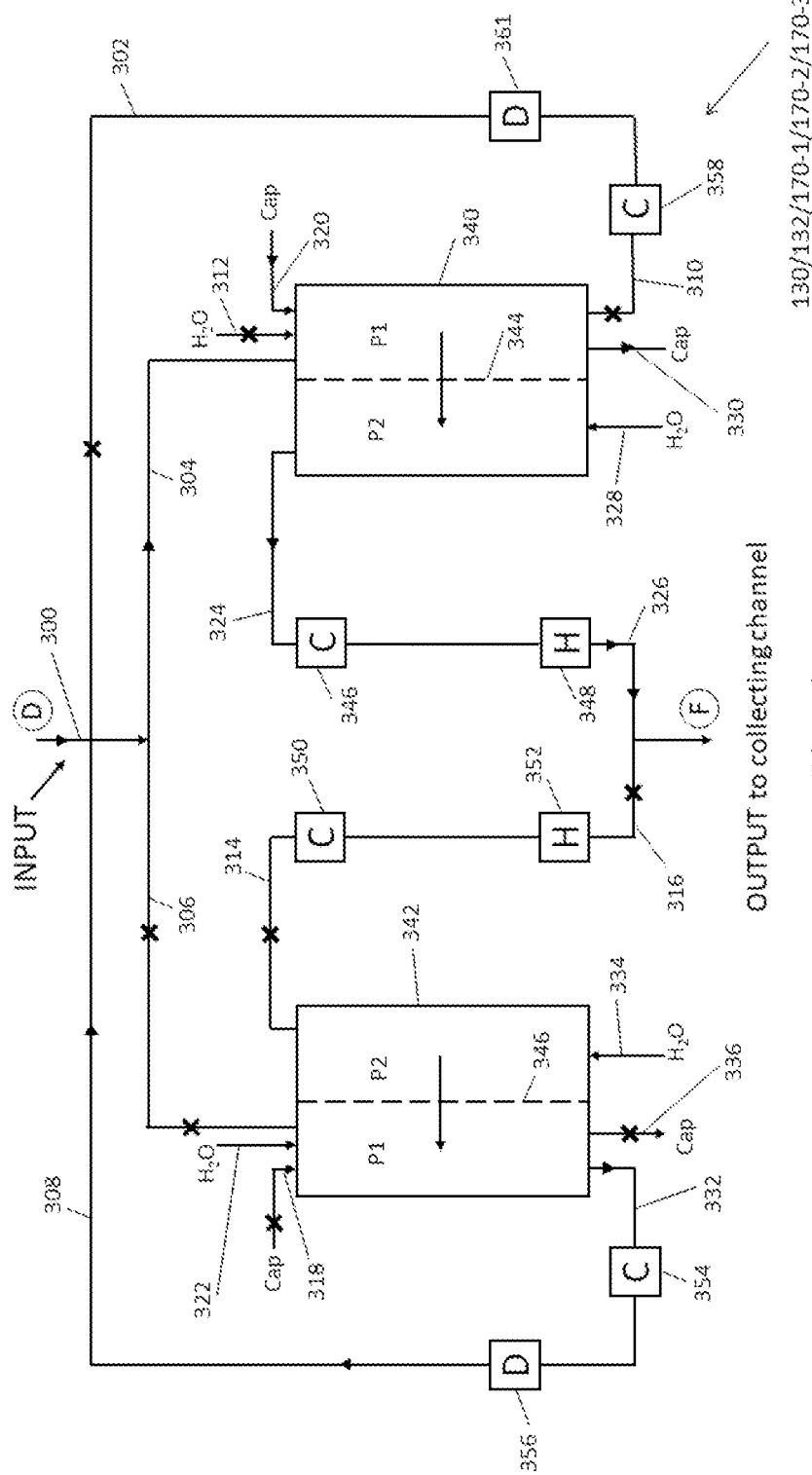
FIG. 3 illustrates an example of a correction unit, in accordance with the present subject matter.

FIG. 3 illustrates an example of a correction unit, in accordance with the present subject matter. Plasma with anions from the ion separation unit 106 or plasma with cations from the ion separation unit 106 or plasma with a specific type of molecules from any of the filtration units, as the case may be, is received in the correction unit via channel 300.

A: For Precise Removal of Excess Entities (Cations or Anions or Specific Type of Molecules)

Plasma enters the correction unit via channel 300. As shown in FIG. 3, the plasma from the channel 300 moves towards channel 304 and then to a cell 340. For said flow of plasma to happen, channels 302, 306, 310, 312, 314, 316, 318, and 336 are kept closed, channels 304, 308, 320, 322, 324, 326, 328, 330, 332, and 334 are kept open, and water is passed to cell 342 via channels 322 (to 342 P1) and via 334 (to 342 P2). The declogged matter from 342 P1 passes out via channel 332 which in turn after concentration at 354 and detection at 356 continues in channel 308 and finally empties into 300. The cell 340 has an SPM 344. The capturing molecule(s) enters the cell 340 P1 through channel 320. The concentration of the capturing molecule(s) depends on the amount of excess entities to be removed from the plasma. The capturing molecules(s) with entities captured thereto do not pass through the SPM 344 and are thus retained in chamber P1 of the cell 340 and exited through channel 330. (Channel 330 carrying captured entities and capturing molecules empty into waste chamber (not shown in FIG. 3)) Minimal but suitable water is passed through chamber P2 of the cell 340 from channel 328. The uncaptured entities get filtered to P2 and exited via channel 324 towards a concentration unit 346. The output of the concentration unit 346 is directed to a holding unit 348 which in turn empties into the collecting channel 180 via channel 326.

B: For Correction of any Entity

For correction of any entity with low concentration, the precise amount can be added to the exit of relevant detection unit detecting the deficiency. Or alternatively the deficiencies can be corrected at the end in collecting channel 180. In FIG. 1, where the collecting channel 180 is a suitable place to add a precise amount to correct low entity.

As described for the ion separation unit 106, the SPM 344 of the cell 340 may get clogged, depending on the properties of the SPM 344 and the molecular load. As shown in FIG. 3, the correction unit also has two parallel identical cells 340 and 342, such that while one of them is filtering, the other one is getting declogged. Each of the units 340 and 342 has a respective SPM 344 and 346. For using the cell 340 for filtering and for declogging the cell 342, the channels 302, 306, 310, 312, 314, 316, 318, and 336 are kept closed, channels 304, 308, 320, 322, 324, 326, 328, 330, 332, and 334 are kept open, and water is passed to cell 342 via channel 322 (to 342 P1) and via 334 (to 342 P2) such that the pressure in 342 P2 is greater than 342 P1. The declogged matter from 342 P1 exits via channel 332 which continues to channel 308 which in turn empties into channel 300. Alternately, for using the cell 342 for filtering and for declogging the cell 340, the channels 302, 306, 310, 312, 314, 316, 318, and 336 are kept open, channels 304, 308, 320, 322, 324, 326, 328, 330, 332, and 334 are kept closed, and water is passed to cell 340 via channel 312 (to 340 P1) and via 328 (to 340 P2) such that pressure in 340 P2 is greater than 340 P1. The declogged matter from 340 P1 exits via channel 310 which after concentration at 358 and detection at 361 continues to 302 and which in turn empties into channel 300. Like for the cell 340, the channel 314 from the cell 342 is connected to a concentration unit 350 and a holding unit 352 connecting to the channel 316 to the collecting channel 180.

Figure 4:
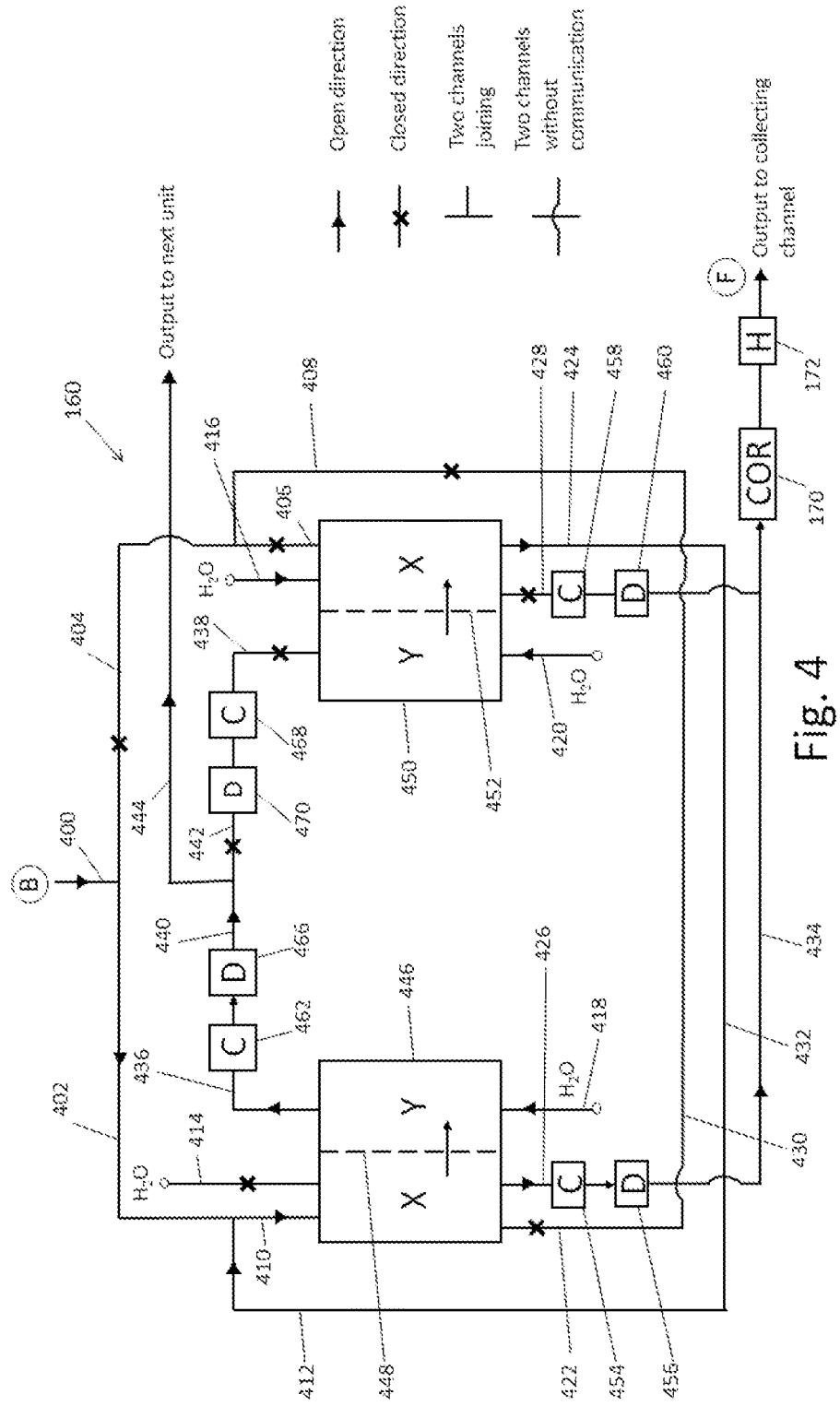
FIG. 4 illustrates an example of a filtration unit, in accordance with the present subject matter.

Configuration of the Filtration Unit 160-1/160-2/160-3:

FIG. 4 illustrates an example of a filtration unit 160, in accordance with the present subject matter. The ion free plasma from the ion separation unit 106, or the plasma, i.e., the filtrate Y1, Y2, Y3, or so on, from a previous filtration unit, as the case may be, is received via channel 400, as shown in FIG. 4.

As shown in FIG. 4, the plasma from the channel 400 moves towards channel 402 and then to a cell 446. For said flow of plasma to happen, channels 404, 406, 408, 414, 422, 428, 430, 438 and 442 are kept closed, channels 400, 402, 410, 412, 418, 424, 426, 432, 434, 436, 440, and 444 are kept open. The solution is passed to 446 C1 via 410 and water is passed through the cell 446 C2 from channels 418. The detectable exit 446 C1 via 426 whereas filtrate exits 446 C2 via 436. Water is passed to cell 450 via channel 416 to 450 C1 and via 420 to 450 C2 such that the pressure in 450 C2 is higher than 450 C1 so that clogging matter on SPM 452 is declogged and exits 450 C1 via 424. 424 continues with 432 which is continuous with 412 which finally empties into 410. The cell 446 has an SPM 448. The SPM 448 is such that molecules X (e.g., X1, X2, X3, and so on, as the case may be) do not pass through the SPM 448 and the remaining molecules Y (Y1, Y2, Y3, and so on, as the case may be) in the plasma pass through the SPM 448. The molecules X are thus retained in plasma entering chamber of the cell 446 and exit through channel 426. The contents of channel 426 are concentrated in 454 and then detected by a detection unit 456 and then continue in channel 434 which in turn empties in corrector 170. Minimal but suitable water is passed through 446 C2 via channel 418 such that pressure and concentration gradient in 446 C1 is higher than 446 C2 so that the filtrate Y across SPM 448 exits 446 C2 via channel 436 towards a concentration unit 462. The output of the concentration unit 462 is directed to a detection unit 466, and the output of the detection unit 466 is directed via channel 444 to a next filtration unit or to the collecting channel 180, as the case may be.

The molecules X from the channel 426 are directed to a concentration unit 454. The output of the concentration unit 454 is directed to a detection unit 456, and the output of the detection unit 456 is directed via channel 434 to the correction unit 170 and further to the holding unit 172 (finally to the collecting channel 180.

As described for the ion separation unit 106 and for the correction unit, the SPM 448 of the cell 446 may get clogged, depending on the properties of the SPM 448 and the molecular load. As shown in FIG. 4, the filtration unit also has two parallel identical cells 446 and 450, such that while one of them if filtering, the other one is getting declogged. Each of the units 446 and 45042 has a respective SPM 448 and 452. For using the cell 446 for filtering and for declogging the cell 450, the channels 404, 406, 408, 414, 422, 428, 430, 438 and 442 are kept closed, channels 400, 402, 410, 412, 418, 424, 426, 432, 434, 436, 440, and 444 are kept open and Water is passed to cell 450 via channel 416 to 450 C1 and via 420 to 450 C2 such that the pressure in 450 C2 is higher than 450 C1 so that clogging matter on SPM 452 is declogged and exits 450 C1 via channel 424 Alternately, for using the cell 450 for filtering and for declogging the cell 404, 406, 408, 414, 422, 428, 430, 438 and 442 are opened and channels 400, 402, 410, 412, 418, 424, 426, 432, 434, 436, 440, and 444 are kept closed. Water is passed to the cell 450 C2 via channel 420 and solution enters 450 C1 via channel 406 such that because of pressure and concentration gradient along with properties of SPM 452, the resulting filtrate leaves 450 C2 via channel 438. The detectable retained in 450 C1 exits via channel 428. Meanwhile water enters 446 C2 via channel 418 and 446 C1 via channel 414 such that the pressure in 446 C2 is higher than 446 C1 so that the clogging matter on SPM 448 on the 446 C1 side is dislodged and the same exits 446 C1 via channel 422 which continues with channel 430 which continues with channel 408 and which finally empties into channel 406. Like for the cell 446, each of the channels 428 and 438 from the cell 450 is connected to a respective concentration unit 458 and 468 and a respective detection unit 460 and 470. Channel 442 from the detection unit 470 is connected to the channel 444. The output of the detection unit 460 is connected to the correction unit 170.

Figure 5:
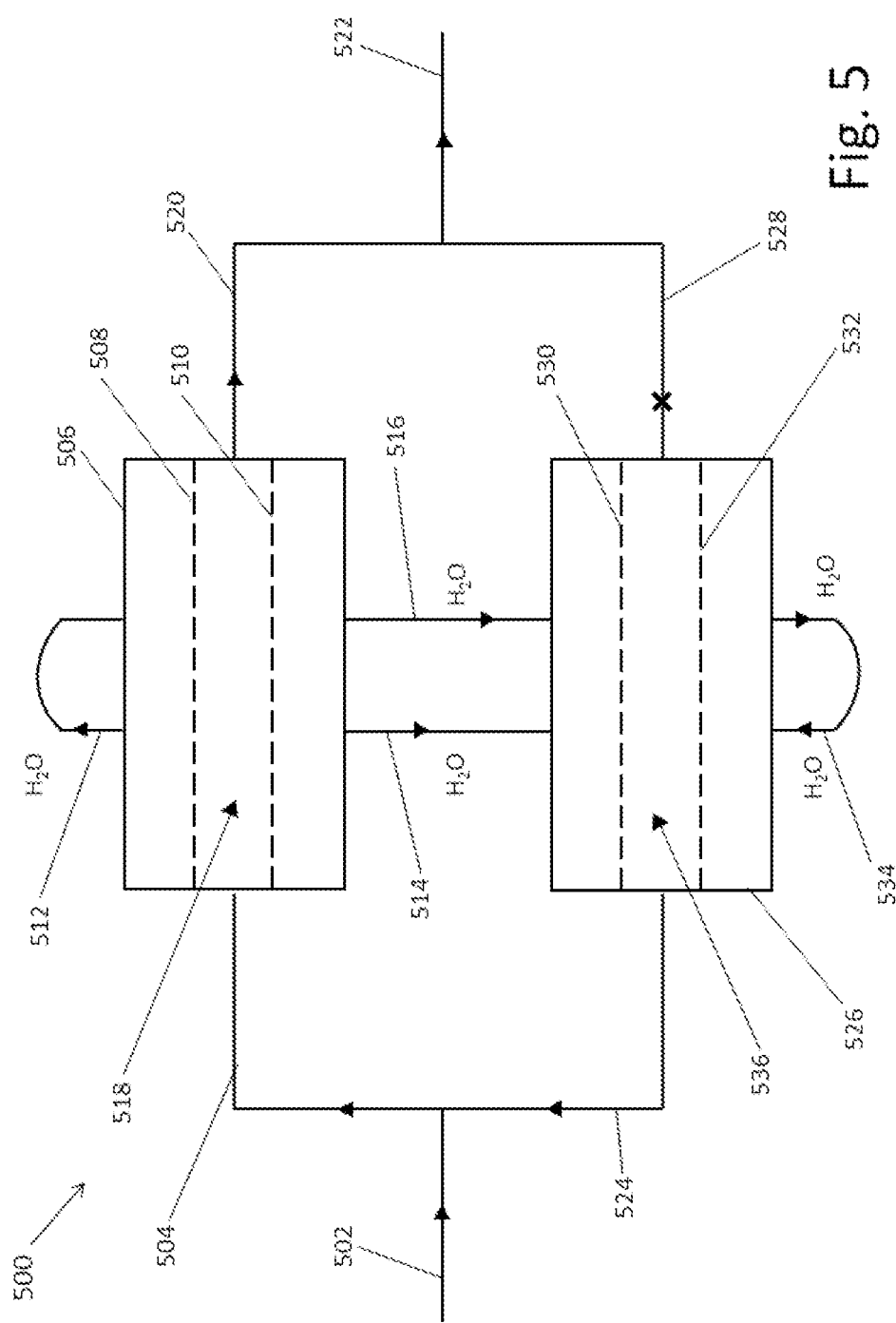
FIG. 5 illustrates an example of a concentration unit, in accordance with the present subject matter.

Configuration of the Concentration Unit:

FIG. 5 illustrates an example of a concentration unit 500, in accordance with the present subject matter. In the concentration unit 500, a precise amount of water is pumped out of the input plasma, i.e., the plasma that enters the concentration unit 500.

The plasma with molecules suspended in water enters the concentration unit 500 via channel 502. The input plasma moves towards a cell 506 via channel 504. In the cell 506, there is a symmetrical arrangement of SPMs 508 and 510, as shown in FIG. 5 such that only water from the cell is able to pass through the SPMs 508 and 510 to the exit channels 514 and 516.

The high but variable/controllable osmotic pressure is generated by high concentration of suitable molecules such that the said molecules are confined only and only to the area between SPMs 508 and 510 outer walls of unit 506. Similarly, the said molecules are confined only and only to the area between SPMs 530 and 532 outer walls of unit 526. In addition, a suitable negative pressure can be applied at exit channels 512/514/516 to expedite removal of water. The removed water can be circulated within the concentration unit 500 or to another unit of the blood analysis system 360. The concentrated plasma from the area 518 of the cell 506 exits via channels 520 and 522, and moves to a further unit, as the case may be. Similar to other units with SPMs an identical unit is placed parallel to 506 which is 526 as shown in the figure such that when 506 is functioning as primary unit for the removal of water unit 526 is getting declogged which is facilitated by closure of channel 528 and pumping of water into 526 such that clogging material on SPMs 530 and 532 is dislodged and collected in 536 from where it is routed back to the primary unit 506 via channel 524.

Configuration of the Detection Unit:

With the ultimate aim of separating all the molecular and ionic entities in blood and measuring the concentration of each in real time in a manner keeping the said entities suitable for reinfusion back to the subject after combining them back again to reconstitute plasma/serum or whole blood, other approaches can be utilized in addition to SPM either in isolation or various combinations. The other approaches may include the following:
  i) Centrifugation including ultracentrifugation (Centri): However it may be time consuming;
  ii) EMF of varying strengths at different stages (EMF)

Therefor the combinations may be (a) SPM+Centri+EMF, (b) SPM+EMF; and (c) EMF+Centri.

A detection unit is used for measuring the concentration of any one type of molecules. The molecules are suspended in water. Let water flow in a channel with a diameter 'd' at a flow rate 'r'. The detecting unit comprises: a source of electromagnetic waves (EMV) or field (EMF) or voltage V of different suitable values; and a detector located opposite to the source measuring changes in either EMV, EMF or V. The changes are going to be a function of the number of water molecules, the flow rate 'r', and the diameter 'd' of the channel. The changes under given conditions can be quantified.

Let's assume now that there are N number of single type molecules uniformly distributed in a given volume of water flowing past the detection unit outlined above. The changes in EMV, EMF or V now are going to be different which in turn are going to be function of concentration of single type of molecules. The changes and corresponding concentrations can be standardized.

Any non-chemical method such as ultraviolet/infrared/visible spectroscopy, absorbance, transmission, impedance, conductivity, selective lasers or combinations of any of these as well as other similar methods can be utilized as long as no structural change is made to the detectable/s. Or even, if any changes are made those must be reversible.

Last option would be chemical reaction however it too must be completely reversible. Since the detectable/s, to be detected, are suspended in water and in continuous flow, the said detectable/s are likely to be highly diluted and therefore it may be challenging to measure the concentration by using methods mentioned above.

The solution would be to 'concentrate' the detectable using the concentration unit, whereby a suitable amount of water is removed. One can then use an appropriate spectroscopic technique such as magnetic resonance or laser spectroscopy or IR or UV or a combination of them, to obtain the relative concentrations or percentages of molecules depending upon the knowledge about the types of molecules present with in the solution. Relative concentrations of different entities are not going to yield the absolute values. Therefore, before detection a known quantity of either inert molecule or a molecule with no adverse effect to the patient or a molecule that can be subsequently captured and removed may be added. The relative percentages of different molecules can be converted into absolute values based on the known concentration of introduced entity.

FIG. 6 illustrates an example of a detection unit 600, in accordance with the present subject matter. The underlying principle to reduce the requirement of complex algorithms would be to reduce the number and/or types of molecules. This can be achieved by progressive bifurcation of the main channel 602 carrying the detectable with bifurcated channels 604, 606, . . . , each of the two bifurcated channels having equal probability of receiving molecular load from the input channel. Thus, each of the two bifurcated channels carry half or 50% load of the original amount being carried by the input channel. A spectroscopy unit is placed at each of the channels 602, 604, 606, . . . such that concentration of molecules in each channel can be calculated in relation to the molecules in any other channel. Post detection the channels can converge as shown in FIG. 6. The number of bifurcations may be directly proportional to the molecular load and the number of types of molecules. The number of bifurcations may also likely to be dictated by sensitivity of detectors.

Limitations:

It may not be possible to completely filter out a molecule. However, at a given flow rate, pressure, characteristics of SPM with or without EMF the fraction of molecules filtered out would be a function of factors mentioned above and initial concentration. During experimentation and standardization, a graph can be made with suitable values of factors mentioned above and the said graph can be used to calculate the actual concentration of molecular or inion entities under consideration.

The blood analysis system 360 due to its vastness may or may not be usable in regular hospitals. The blood analysis system 360 can be used in its entirety or else it can be contracted such that only a narrow range of detectable are isolated and measured/manipulated. For patients with septicemia only Corrector may be employed to remove microbial products and excess proinflammatory cytokines. The patients in Intensive care units can benefit greatly just by making use of ion separation unit. Limited modules can be used for numerous medical conditions as some of them are listed in the introduction.

Fabrication of the Blood Analysis System 360:

Since this kind of system has never been imagined before, it has to be built from the scratch. The blood analysis system 360 may be first standardized on medium to large mammals. Alternatively, expired human blood from blood banks or human plasma can be used.

One of the mandates of the blood analysis system 360 is to measure the detectables in real time using non-chemical methods. Whatever data is obtained using such methods has to be compared with some Gold standards. Therefore, the first step would be to take a blood volume with known concentrations of as many molecules and ionic entities as possible. The volume required via chemical methods would be appreciable if one were to ensure consistency and true value. It has to be kept in mind that even with the chemical methods depending on the equipment, methods, kits or personnel, the variation of up to 10% is not unusual even if identical sample is used. The variation appears to be unavoidable but acceptable enough to base treatment of patients in spite of it.

Second step would be to ensure the readings of non-chemical methods employed in the blood analysis system 360 and compare the results with the chemical methods/NMR, note down the differences, if any, and ascertain if the differences have a predictable pattern or are random or chaotic. The data gleaned from chemical/NMR and non-chemical methods have to be compared at each step of the system without exception. Since the rate of filtration and proportion of total molecules filtered is determined by variables such as SPM pore size, SPM pore density, SPM surface area, Rate of flow of solution in C, Pressure in C1 and C2, Number of types of molecules/unit volume, Number of each type of molecules with unique MW/unit volume, Number of anions with different valences/unit volume, Number of cations with different valences/unit volume, and Viscosity (V) of fluid entering various units of the blood analysis system 360.

During calibration all the above or some of them may have to be used with different properties (in case of SPMs) or values (in case of concentrations and pressures) till a useful reproducible pattern emerges. The process has to be repeated till statistically relevant results are obtained and reproducible algorithms are delineated.

Applications/Uses:

The applications of the blood analysis system 360 are diverse and will expand with time. Few of the experimental and therapeutic uses are as follows:

Experimental Uses

1. Accurate, real time and continuous measurement of all molecular/ionic entities in blood without the use of any chemical reactions will be helpful to study the trends in normal growth and aging of all mammals including humans.
2. It will elucidate trends of all disease processes as reflected in the composition of blood. It will clarify the demarcation of the state of health from the state of disease by studying these trends in all mammals.
3. It will help understand and define the process of dying. It will help mark the beginning of a state of irreversibility during dying and will possibly indicate ways to shift/change the point of irreversibility in critically ill patients.
4. It will help to describe with greater precision the changes induced in the body during iatrogenic interventions like use of drugs, use of anesthetic agents, hypothermia, hyperthermia, etc.
5. It will contribute greatly to our understanding of 'intraoperative physiology' with detailed and precise information of fluctuations of all molecular/ionic parameters in blood during anesthesia and surgery. Such data may potentially alter the definition of 'high risk patient'.

Therapeutic Uses:

A) Uses of Chemical Capture:
1. DKA/HSS: Removal of excess glucose with titration of all other molecular/ionic entities in blood.
2. Bites, Venoms, Stings, Drug overdoses, Accidental/Intentional poisoning, Toxin mediated injury: Removal of unwanted entity from blood without subjecting the patient to any drug or chelator.
3. Electrolyte imbalance: Titration of electrolytes to precise levels without the use of drugs, resins etc.
4. Renal impairment or renal failure/Azotemia or Uremia: Titration of all molecular/ionic entities like creatinine, urea, potassium etc. to precise levels without the use of anticoagulants and without drawing a significant about of blood from the body at any given point of time thereby not subjecting the patient to iatrogenic hypotension.
5. Kernicterus due to unconjugated hyperbilirubinemia: Removal of bilirubin
6. Metabolic encephalopathies such as hepatic, renal/uremic, pulmonary encephalopathy: Titration of the undesired molecular/ionic entity
7. Acute autoimmune conditions like Hemolytic uremic syndrome, Guillian-barre syndrome etc: Complete removal of the implicated antibodies.
8. Acute flare ups of all autoimmune conditicated antibodies ions like Rheumatoid arthritis, SLE, Acute rheumatic fever etc.: Complete removal of implicated antibodies.
9. Pancreatitis and it's complications: Prevention of pancreatitis in high risk patients by removal of offending agents like implicated drugs, triglycerides, infectious agents etc. Prevention of complications of pancreatitis like ARDS by removal of leaked/spilled over proteases from blood.
10. Endocrine crises such as Thyroid storm, Pheochromocytoma, SIADH etc.: Titration of the implicated hormone.
11. Diseases with dysregulation/compensatory overdrive of the Renin Angiotensie aldosterone system (RAAS) like Acute decompensated heart failure, Hypertensive emergency of any etiology, Hypotensive crisis: Titration of the RAAS along with titration of Vasopressin, Atrial and Brain natriuretic peptide etc.
12. Metabolic disorders of dysregulated excretion like Hemochromatosis, Wilson's disease etc.: Removal of implicated agent.
13. Infectious condition including all bacterial, fungal and viral infections including HIV/AIDS: Complete removal from all bacterial, fungal and viral particles from blood thereby largely precluding the need for antimicrobials.

14. It will be a tool to maintain 'intraoperative' and 'intra-ICU' steady state with continuous, precise measurement and prompt titration of all molecular/ionic entities in blood.

B) Uses of Selective Infusion and Capture at Different Sites:

1. Fluoroscopic infusion of thrombolytics such as tissue plasminogen activators into the coronary arteries following myocardial infarction with prompt extraction of the thrombolytic from the carotid arteries to reduce the risk of intracranial hemorrhage. This will markedly reduce exclusion criteria of thrombolytic interventions.

2. Selective infusion of chemotherapeutic agents through the arterial end of the intended site of action with extraction from the venous end thereby negating the inadvertent adverse effects of such drugs at all other sites.

3. Removal of nephrotoxic drugs from the renal artery and hepatotoxic drugs from the hepatic artery and portal vein thereby allowing such drugs to be used in adequate doses in patients with compromised kidneys and livers respectively.

A system would be desirable and of significant value that can detect concentration of all the detectables in blood in real time without patient/subjects/animals having to lose any blood in the process. The system would also make it possible to either introduce or extract desired detectable for therapeutic and/or experimental purposes, latter in animal models.

Blood is highly complex fluid containing cellular, molecular and ionic entities therefore in order to achieve the objectives listed above it is imperative that all the constituents are separated or isolated completely or as much as pragmatically possible. The isolation of one type of molecule without chemical reaction from a complex solution is extremely common indeed. Desalination of sea water and reverse osmosis in domestic use for water purification allow only water molecules to pass through whereas rest of the molecules are not. Dialysis on the other hand allow only a few molecules to pass through. All these processes make use of semi-permeable membranes with properties relevant to the situation at hand.

The blood analysis system 360 requires sophisticated control systems, software and extreme precision. The system probably would not have been possible even in the early 21th century but now with significant advances in nanotechnology, precision and computing power it should not be difficult to manufacture the same. The blood analysis system 360 can serve the purpose of not only understanding normal mammalian physiology but also morbid states as reflected in blood. The therapeutic applications are numerous since the blood analysis system 360 is capable of extracting molecular or ionic entities from blood without any drug.

The following description describes an example procedure for analysis of blood for detecting and correcting glucose levels using the blood analysis system 360 as described through FIGS. 1 to 6. The sequence of steps for monitoring and management of a patient (i.e., a subject) of diabetes mellitus with the blood glucose level reaching beyond 600 mg/dl and causing an electrolyte disturbance (abnormal sodium, potassium levels). Conventionally, such patients are managed by drugs, such as insulin, metformin, etc., where the dose of these drugs is adjusted by repeated blood testing of parameters that are to be corrected. Molecular weight of glucose being 180. A molecular weight cut off (MWCO) of an SPM is lowest molecular weight of the solute of which 90% is retained. For instance, an SPM with the MWCO of 180 will retain 90% of the glucose and molecules larger than glucose.

Step 1: The blood of the patient is passed to centrifugation unit 102 via a channel. The channel is made of an inert material similar to what is used in other extracorporeal systems, like dialysis or plasmapheresis. Example materials include, but are not limited to, biocompatible polyvinylchloride or other material.

Step 2. The capturing molecules for chemical capture of calcium ion and/or one or more of the coagulation factors along with complement factors are added into the centrifugation unit 102 prior to the blood entering the centrifugation unit 102. After this, the centrifugation unit 102, with or without incorporated SPM, is operated to centrifuge such that the cellular components with minimal plasma and capturing molecules are separated from majority of plasma with capturing molecules.

Step 3. The cellular components (with or without dilution by physiological fluid) is directed towards a correction unit (not shown in FIG. 1) coupled to the centrifugation unit 102. This correction unit receives the minimal plasma having the capturing molecules and the cellular components from the centrifugation unit 102, which extracts all the capturing molecules from the cellular components and rest of the minimal plasma.

Step 4. The minimal plasma having the separated cellular components is infused back to the patient along with replaced captured molecules and/or ions, and the capturing molecules are discarded.

Step 5. The separated plasma from step 2 is directed to the holding unit 104, where the plasma is diluted with water, if necessary, to control the viscosity of the plasma.

Step 6. The plasma from the holding unit 105 is directed to the ion separation unit 106, where the anions and the cations in the plasma are separated. The separation of the cations, like sodium and potassium, is effected by making use of electrodialysis, where negatively charged SPM 144, 151 of the cell 142, 144, with MWCO of 50, with/without centrifugation, with/without suitable electromagnetic field, is used so that only negatively charged ions (anions) are able to pass through. The filtered cations are directed to a concentration unit (not shown), a detection unit (not shown), and then to the correction unit 132 for correction. Post correction, the cations are directed to the holding unit 158, which are then released to the collecting channel 180. The separation of anions, like chloride, etc., is effected by making use of electrodialysis, where positively charged SPM 125, 150 of the cell 110, 116, with MWCO of 50, with/without centrifugation, with/without suitable electromagnetic field, is used so that only negatively charged ions (anions) are able to pass through. The filtered anions are directed to a concentration unit (not shown), a detection unit (not shown), and the correction unit 130 for correction. Post correction, the anions are directed to the holding unit 156, which are then released to the collecting channel 180.

Step 7. The ion free plasma, with the capturing molecules, from ion separation unit 106 is directed to the filtration unit 160-1, where the SPM with MWCO of 500, with/without centrifugation, with/without suitable electromagnetic field, is used such that the entities with the molecular weight of more than 500 are retained in X1 of the filtration unit 160-1 and the entities with the molecular weight of less than 500 (including glucose with MW of 180) are filtered to Y1 of the filtration unit 160-1. The retained entities in X1 is directed to the correction unit 170-1 for correction or directly to the holding unit 172-1 for further transfer to the collecting channel 180.

Step 8a. The filtrate in Y1 of the filtration unit 160-1 (molecular weight less than 500) is directed to a concentration unit (not shown), followed by a detection unit (not shown), and a correction unit (not shown), where high levels of glucose are corrected. The corrected fluid is directed to a holding unit (not shown) and finally to the collecting channel 180.

Step 8b (optional). The filtrate in Y1 (the molecular weight less than 500) is channeled directly to next unit filtration unit 160-2, bypassing the concentration unit, the detection unit, and the correction unit. In the filtration unit 160-2, each of the cells has a SPM with the MWCO of 300 and with/without centrifugation, with/without suitable electromagnetic field, the filtration unit 160-2 is operated such that the entities with molecular weight of more than 300 are retained in X2 and the entities of molecular weight less than 300 are channeled from Y2 a concentration unit (not shown) followed by a detection unit (not shown). Then the filtrate is channeled to a correction unit (not shown) where high levels of glucose are corrected. The corrected fluid is directed to a holding unit (not shown) and finally to the collecting channel 180. Meanwhile, the retained entities in X2 are directed to a concentration unit (not shown), a detection unit (not shown), and the correction unit 170-2 and then to the holding unit 172-2, or directly to the holding unit 172 bypassing the concentration unit (not shown), the detection unit (not shown), and the correction unit 170-2. From the holding unit 172-2, the entities are released into the collecting channel 180.

Step 8c (optionally). The entities in Y2 (the molecular weight less than 300) is directed to the next filtration unit 160-3, where the SPM with MWCO of 200 is used, and with/without centrifugation, with/without suitable electromagnetic field, the entities with molecular weight of more than 200 are retained in X3 and the entities with molecular weight less than 200 from Y3 are channeled to a detection unit (not shown), where the concentration of glucose measured and then the filtrate is channeled to the correction unit (not shown) where high levels of glucose are corrected. The corrected fluid is directed to a holding unit (not shown) and finally to the collecting channel 180. Meanwhile, the retained entities in X3 are directed to a holding unit (not shown) and finally to the collecting channel 180.

The purpose of sequential filtration units with the SPMs of different MWCOs is to reduce the types of molecules in a given solution so that both the detection and the correction are specific and reliable. It may be possible to get the desirable results after just one filtration unit or none at all.

In an example, the blood analysis system (360) as claimed in claim 1, the blood analysis system (360) comprises a control unit (not shown) to cut-off or cause a flow of plasma and/or cellular component at each channel of the blood analysis system (360) via flow rate pumps (not shown) so as to ensure coordination between all units and eventual reconstitution of plasma before reinfusion back to the subject.

In an example, any channel as shown and described herein is made of an inert material similar to what is used in other extracorporeal systems, like dialysis or plasmapheresis. Example materials include, but are not limited to, biocompatible polyvinylchloride or other material.

First Set of Example Embodiments

In an example, the blood analysis system (360) for analysis and correction of blood of a subject comprises a centrifugation unit (102) to receive blood of a subject. The centrifugation unit (102) is to hold capturing molecules for chemical capture of molecules and/or ions that deactivate at least one of coagulation and complement pathways in the blood; and centrifuge to suspend cellular components with a minimal plasma along with the capturing molecules. The blood analysis system 360 comprises a holding unit (104) coupled to the centrifugation unit (102) to receive plasma with the capturing molecules but without the cellular components from the centrifugation unit (102) and hold the received plasma; and an ion separation unit (106) coupled to the holding unit (104) to receive the plasma from the holding unit (104). The ion separation unit (106) is to separate anions and cations from the received plasma based on electrostatically-charged semi permeable membranes. The blood analysis system 360 further comprises one or more filtration units (160-1, 160-2, 160-3) to receive ion-free plasma with the capturing molecules expelled from the ion separation unit (106) to filter out one or more specific types of molecules from the ion-free plasma for detection and correction, before moving the ion-free plasma having the corrected filtered molecules towards a collecting channel (180) for infusing back to the subject.

In an example, the received plasma is diluted with water in the holding unit (104) to control the viscosity of the received plasma.

In an example, the ion separation unit (106) is to separate the anions before the cations, or separate the cations before the anions.

In an example, the ion separation unit (106) is to separate the anions and the cations from the received plasma with or without at least one of centrifugation and external electromagnetic field.

In an example, the ion separation unit (106) is coupled to the holding unit (104) through a channel (108) to receive the received plasma, and the ion separation unit (106) comprises an anion separation unit and a cation separation unit.

In an example, the anion separation unit comprises a first cell (110) coupled to the channel (108) and having a first semi-permeable membrane (SPM) (125) of a specific molecular weight cut-off that allows the anions to pass through; and a second cell (116) coupled to the channel (108) and having a second SPM (150). The second SPM (150) being the same as the first SPM (125). One of the first cell (110) and the second cell (116) is operated to separate the anions and the other of the first cell (110) and the second cell (116) is operated for declogging. Each of the first cell (110) and the second cell (116) is coupled to a respective concentration unit (112, 118) and a respective detection unit (114, 120) to concentrate and detect, respectively, the filtered anions. The detection unit (114, 120) is coupled to a correction unit (130) to correct a concentration of reconstituted anions expelled from the detection unit (114, 120) before passing the corrected anions towards the collecting channel (180).

In an example, the cation separation unit comprises a third cell (142) coupled to a channel (129) to receive a retentate plasma from the first cell (110) and the second cell (116) and having a third semi-permeable membrane (SPM) (144) of a specific molecular weight cut-off that allows the cations to pass through; and a fourth cell (143) coupled to the channel (129) to receive a retentate plasma from the first cell (110) and the second cell (116) and having a fourth SPM (151). The fourth SPM (151) being the same as the third SPM (144). One of the third cell (142) and the fourth cell (143) is operated to separate the cations and the other of the third cell (142) and the fourth cell (143) is operated for declogging. Each of the third cell (142) and the fourth cell (143) is coupled to a respective concentration unit (146, 152) and a respective detection unit (148, 154) to concentrate and detect, respectively, the filtered cations, and the detection unit (148, 154) is coupled to a correction unit (132) to correct a concentration of reconstituted cations expelled from the detection unit (148, 154) before passing the corrected cations towards the collecting channel (180).

In an example, the first SPM (125), the second SPM (150), the third SPM (144), and the fourth SPM (151) are negatively charged, when the anion separation unit is positioned before the cation separation unit in the ion separation unit (106).

In an example, the first SPM (125), the second SPM (150), the third SPM (144), and the fourth SPM (151) are positively charged, when the cation separation unit is positioned before the anion separation unit in the ion separation unit (106).

In an example, each filtration unit (160-1) comprises a fifth cell (446) coupled to a channel (400) to receive the ion-free plasma from the ion separation unit (106) and having a fifth SPM (448) of a specific molecular weight cut-off that allows molecules of a molecular weight equal to or less than the specific molecular weight cut-off to pass through; and a sixth cell (450) coupled to the channel (400) to receive the ion-free plasma from the ion separation unit (106) and having a sixth SPM (452). The sixth SPM (452) being the same as the fifth SPM (446). One of the fifth cell (446) and the sixth cell (450) is operated to filter the molecules and the other of the fifth cell (446) and the sixth cell (450) is operated for declogging. Chambers on both sides of the fifth and sixth SPMs (448, 452) of each of the fifth cell (446) and the sixth cell (450) are coupled to a respective concentration unit (454, 458, 462, 468) and a respective detection unit (456, 460, 466, 470) to concentrate and detect, respectively, the retentate and filtrate molecules. The detection unit (456, 460), coupled to a retentate side of the fifth and sixth SPMs (448, 452) of the corresponding chamber, is coupled to a correction unit (170-1, 170-2, 170-3) to correct a concentration of reconstituted molecules expelled from the detection unit (456, 460) before passing the corrected molecules towards the collecting channel (180), and the detection unit (466, 470), coupled to a filtrate side of the fifth and sixth SPMs (448, 452) of the corresponding chamber, is coupled to a subsequent filtration unit (160-2, 160-3) for sequential filtration of molecules of a specific molecular weight less than the specific molecular weight cut-off associated with a previous filtration unit (160-1).

In an example, each of the correction units (130, 132, 170-1, 170-2, 170-3) comprises a seventh cell (340) coupled to a channel (300) to receive plasma with the capturing molecules and with molecules and/or with ions that are to be corrected and having a seventh SPM (344) of a specific molecular weight cut-off that allows molecules of a molecular weight equal to or less than the specific molecular weight cut-off to pass through; and an eighth cell (342) coupled to the channel (300) to receive plasma with the capturing molecules and with molecules and/or ions that are to be corrected and having an eighth SPM (346). The eighth SPM (346) being the same as the seventh SPM (344). One of the seventh cell (340) and the eighth cell (342) is operated to separate the molecules and/or ions and/or the capturing molecules and the other of the seventh cell (340) and the eighth cell (342) is operated for declogging. The capturing molecules are removed from one of the seventh cell (340) and eighth cell (342) and discarded. Chambers on a retentate side of the seventh and eighth SPMs (344, 346) of each of the seventh cell (340) and the eighth cell (342) are coupled to a channel (320, 318) to receive capturing molecules having a concentration depending on an amount of excess molecules and/or ions that are to be captured and removed from the plasma via the chambers on the retentate side, and are coupled to a respective concentration unit (354, 358) and a respective detection unit (356, 360) to concentrate and detect, respectively, un-captured retentate molecules and/or ions during declogging of the seventh cell (340) or the eighth cell (342) or to correct a concentration of the un-captured retentate molecules and/or ions based on the detection. Chambers on a filtrate side of the seventh and eighth SPMs (344, 346) of each of the seventh cell (340) and the eighth cell (342) are coupled to a respective concentration unit (346, 350) and a respective holding unit (348, 352) to concentrate and hold, respectively, filtrate molecules and/or ions before passing the filtrate molecules and/or ions towards the collecting channel (180).

In an example, each concentration unit comprises a ninth cell (506) with a symmetrical arrangement of SPMs (508, 510) and a channel (504) to receive plasma in a region between the symmetrical arrangement of SPMs (508, 510); a tenth cell (526) with a symmetrical arrangement of SPMs (530, 532) and a channel (524) to receive plasma in a region between the symmetrical arrangement of SPMs (530, 532); and an arrangement to allow water to circulate through the ninth cell (506) and the tenth cell (526), where one of the ninth cell (506) and the tenth cell (526) is operated to increase a concentration of the plasma and the other of the ninth cell (506) and the tenth cell (526) is operated for declogging, where the water is circulated to create an osmotic pressure in the regions between the symmetrical arrangement of SPMs (508, 510, 530, 532) and confine concentrated plasma to one of an area 518 and an area 536 that is being operated for concentration of the plasma.

In an example, each detection unit comprises a plurality of pairs of bifurcation channels (604, 606, 608, 610, 612, 614, . . . ), where each pair of bifurcation channels (606, 608) is to bifurcate plasma from a previous bifurcation channel (604) or from an inlet channel (602), through which plasma for detection of molecules is received, into two substantially equal plasma streams; at least one of a spectroscopy unit and a chemical reaction-based measurement unit installed in each bifurcation channel to determine a concentration of the molecules and/or the ions in the respective bifurcation channel; and a plurality of converging channels (632, 634, 636, 638, . . . ), where each converging channel is to combine two plasma streams from a pair of bifurcation channels or from two converging channels into a single stream.

In an example, the detection unit is to determine whether the detected concentration of the molecules and/or the ions is less than or more than a predefined value; in response to detecting that the concentration is less than the predefined value, add a specific amount of the molecules and/or the ions to match the predefined value; and in response to detecting that the concentration is more than the predefined value, provide information to the correction unit about an amount of the molecules and/or the ions that are in excess, where the correction unit is to operate the channel (318, 320) to provide a specific amount to capturing molecules into one of the seventh cell (340) and eighth cell (342) to remove the excess amount of the molecules and/or the ions.

In an example, the blood analysis system (360) comprising a correction unit coupled to the centrifugation unit (102) to receive the minimal plasma having the capturing molecules and the cellular components from the centrifugation unit (102), where the correction unit is to extract the capturing molecules from the minimal plasma.

In an example, the minimal plasma having the cellular components is infused back to the subject along with replaced captured molecules and/or ions, and where the extracted capturing molecules are discarded.

In an example, the minimal plasma having the cellular components are suspended in an isotonic solution, and optionally with oxygen and glucose, before infusing back of the subject.

In an example, the blood analysis system (360) comprises an SPM and/or a centrifuge to separate platelets from the minimal plasma; a detection unit to receive the separate platelets and count the platelets; and a correction unit to correct the count of the platelets before infusing the minimal plasma with the corrected platelets to the subject.

In an example, the minimal plasma, after separating the platelets, is ultra-centrifuged to separate granulocytes from the minimal plasma, where the blood analysis system (360) comprises a detection unit to count the granulocytes; and a correction unit to correct the count of the granulocytes, before infusing the minimal plasma with the corrected granulocytes to the subject.

In an example, the minimal plasma, after separating the platelets, is ultra-centrifuged to separate red blood cells (RBCs) from the minimal plasma, where the blood analysis system (360) comprises a detection unit to count the RBCs; and a correction unit to correct the count of the RBCs, before infusing the minimal plasma with the corrected RBCs to the subject.

In an example, molecules and/or ions, equivalent to the molecules and/or the ions captured by the discarded capturing molecules, are added before infusing the plasma back to the subject.

In an example, the blood analysis system (360) comprises a control unit to cut-off or cause a flow of plasma and/or cellular component at each channel of the blood analysis system (360) via flow rate pumps.

Second Set of Example Embodiments

In an example, the blood analysis system (360) for analysis and correction of blood of a subject comprises a centrifugation unit (102) to receive blood of a subject, where the centrifugation unit (102) is to hold capturing molecules for chemical capture of molecules and/or ions that deactivate at least one of coagulation and complement pathways in the blood; and centrifuge to suspend cellular components with a minimal plasma along with the capturing molecules. The blood analysis system 360 comprises a correction unit coupled to the centrifugation unit (102) to receive the minimal plasma having the capturing molecules and the cellular components from the centrifugation unit (102), where the correction unit is to extract the capturing molecules from the minimal plasma, prior to infusing the minimal plasma having the cellular components along with replaced captured molecules and/or ions back to the subject and discarding the extracted capturing molecules.

In an example, the minimal plasma having the cellular components are suspended in an isotonic solution, and optionally with oxygen and glucose, before infusing back of the subject.

In an example, the blood analysis system (360) comprises an SPM and/or a centrifuge to separate platelets from the minimal plasma; a detection unit to receive the separate platelets and count the platelets; and a correction unit to correct the count of the platelets before infusing the minimal plasma with the corrected platelets to the subject.

In an example, the minimal plasma, after separating the platelets, is ultra-centrifuged to separate granulocytes from the minimal plasma, and where the blood analysis system (360) comprises: a detection unit to count the granulocytes; and a correction unit to correct the count of the granulocytes, before infusing the minimal plasma with the corrected granulocytes to the subject.

In an example, the minimal plasma, after separating the platelets, is ultra-centrifuged to separate red blood cells (RBCs) from the minimal plasma, and where the blood analysis system (360) comprises: a detection unit to count the RBCs; and a correction unit to correct the count of the RBCs, before infusing the minimal plasma with the corrected RBCs to the subject.

In an example, the blood analysis system (360) comprises: a holding unit (104) coupled to the centrifugation unit (102) to receive plasma with capturing molecules but without the cellular components from the centrifugation unit (102) and hold the received plasma; one or more filtration units (160-1, 160-2, 160-3) to receive the plasma with the capturing molecules expelled from the holding unit (104) to filter out one or more specific types of molecules from the plasma for detection and correction, before moving the ion-free plasma having the corrected filtered molecules towards a collecting channel (180) for infusing back to the subject.

In an example, the received plasma is diluted with water in the holding unit (104) to control the viscosity of the received plasma.

In an example, the blood analysis system (360) comprises an ion separation unit (106) between the holding unit (104) and the at least one filtration unit (160-1, 160-2, 160-3) to receive the plasma from the holding unit (104), the ion separation unit (106) is to separate anions and cations from the received plasma based on electrostatically-charged semi permeable membranes.

In an example, the ion separation unit (106) is to: separate the anions before the cations, or separate the cations before the anions.

In an example, the ion separation unit (106) is to separate the anions and the cations from the received plasma with or without at least one of centrifugation and external electromagnetic field.

In an example, the ion separation unit (106) is coupled to the holding unit (104) through a channel (108) to receive the received plasma, and the ion separation unit (106) comprises an anion separation unit and a cation separation unit.

In an example, the anion separation unit comprises: a first cell (110) coupled to the channel (108) and having a first semi-permeable membrane (SPM) (125) of a specific molecular weight cut-off that allows the anions to pass through; and a second cell (116) coupled to the channel (108) and having a second SPM (150), where the second SPM (150) being the same as the first SPM (125). One of the first cell (110) and the second cell (116) is operated to separate the anions and the other of the first cell (110) and the second cell (116) is operated for declogging. Each of the first cell (110) and the second cell (116) is coupled to a respective concentration unit (112, 118) and a respective detection unit (114, 120) to concentrate and detect, respectively, the filtered anions, and the detection unit (114, 120) is coupled to a correction unit (130) to correct a concentration of reconstituted anions expelled from the detection unit (114, 120) before passing the corrected anions towards the collecting channel (180).

In an example, the cation separation unit comprises: a third cell (142) coupled to a channel (129) to receive a retentate plasma from the first cell (110) and the second cell (116) and having a third semi-permeable membrane (SPM) (144) of a specific molecular weight cut-off that allows the cations to pass through; and a fourth cell (143) coupled to the channel (129) to receive a retentate plasma from the first cell (110) and the second cell (116) and having a fourth SPM (151), where the fourth SPM (151) being the same as the third SPM (144). One of the third cell (142) and the fourth cell (143) is operated to separate the cations and the other of the third cell (142) and the fourth cell (143) is operated for declogging. Each of the third cell (142) and the fourth cell (143) is coupled to a respective concentration unit (146, 152) and a respective detection unit (148, 154) to concentrate and detect, respectively, the filtered cations. The detection unit (148, 154) is coupled to a correction unit (132) to correct a concentration of reconstituted cations expelled from the detection unit (148, 154) before passing the corrected cations towards the collecting channel (180).

In an example, the first SPM (125), the second SPM (150), the third SPM (144), and the fourth SPM (151) are negatively charged, when the anion separation unit is positioned before the cation separation unit in the ion separation unit (106).

In an example, where the first SPM (125), the second SPM (150), the third SPM (144), and the fourth SPM (151) are positively charged, when the cation separation unit is positioned before the anion separation unit in the ion separation unit (106).

In an example, each filtration unit (160-1) comprises: a fifth cell (446) coupled to a channel (400) to receive the plasma and having a fifth SPM (448) of a specific molecular weight cut-off that allows molecules of a molecular weight equal to or less than the specific molecular weight cut-off to pass through; and a sixth cell (450) coupled to the channel (400) to receive the plasma and having a sixth SPM (452), where the sixth SPM (452) being the same as the fifth SPM (446), where one of the fifth cell (446) and the sixth cell (450) is operated to filter the molecules and the other of the fifth cell (446) and the sixth cell (450) is operated for declogging, where chambers on both sides of the fifth and sixth SPMs (448, 452) of each of the fifth cell (446) and the sixth cell (450) are coupled to a respective concentration unit (454, 458, 462, 468) and a respective detection unit (456, 460, 466, 470) to concentrate and detect, respectively, the retentate and filtrate molecules, where the detection unit (456, 460), coupled to a retentate side of the fifth and sixth SPMs (448, 452) of the corresponding chamber, is coupled to a correction unit (170-1, 170-2, 170-3) to correct a concentration of reconstituted molecules expelled from the detection unit (456, 460) before passing the corrected molecules towards the collecting channel (180), and where the detection unit (466, 470), coupled to a filtrate side of the fifth and sixth SPMs (448, 452) of the corresponding chamber, is coupled to a subsequent filtration unit (160-2, 160-3) for sequential filtration of molecules of a specific molecular weight less than the specific molecular weight cut-off associated with a previous filtration unit (160-1).

In an example, each of the correction units (130, 132, 170-1, 170-2, 170-3) comprises: a seventh cell (340) coupled to a channel (300) to receive plasma with the capturing molecules and with molecules and/or ions that are to be corrected and having a seventh SPM (344) of a specific molecular weight cut-off that allows molecules of a molecular weight equal to or less than the specific molecular weight cut-off to pass through; and an eighth cell (342) coupled to the channel (300) to receive plasma with the capturing molecules and with molecules and/or ions that are to be corrected and having an eighth SPM (346), where the eighth SPM (346) being the same as the seventh SPM (344), where one of the seventh cell (340) and the eighth cell (342) is operated to separate the molecules and/or ions and/or the capturing molecules and the other of the seventh cell (340) and the eighth cell (342) is operated for declogging, where the capturing molecules are removed from one of the seventh cell (340) and eighth cell (342) and discarded. Chambers on a retentate side of the seventh and eighth SPMs (344, 346) of each of the seventh cell (340) and the eighth cell (342) are coupled to a channel (320, 318) to receive capturing molecules having a concentration depending on an amount of excess molecules and/or ions that are to be captured and removed from the plasma via the chambers on the retentate side, and are coupled to a respective concentration unit (354, 358) and a respective detection unit (356, 360) to concentrate and detect, respectively, un-captured retentate molecules and/or ions during declogging of the seventh cell (340) or the eighth cell (342) or to correct a concentration of the un-captured retentate molecules and/or ions based on the detection, where chambers on a filtrate side of the seventh and eighth SPMs (344, 346) of each of the seventh cell (340) and the eighth cell (342) are coupled to a respective concentration unit (346, 350) and a respective holding unit (348, 352) to concentrate and hold, respectively, filtrate molecules and/or ions before passing the filtrate molecules and/or ions towards the collecting channel (180).

In an example, each concentration unit comprises a ninth cell (506) with a symmetrical arrangement of SPMs (508, 510) and a channel (504) to receive plasma in a region between the symmetrical arrangement of SPMs (508, 510); a tenth cell (526) with a symmetrical arrangement of SPMs (530, 532) and a channel (524) to receive plasma in a region between the symmetrical arrangement of SPMs (530, 532); and an arrangement to allow water to circulate through the ninth cell (506) and the tenth cell (526), where one of the ninth cell (506) and the tenth cell (526) is operated to increase a concentration of the plasma and the other of the ninth cell (506) and the tenth cell (526) is operated for declogging, where the water is circulated to create an osmotic pressure in the regions between the symmetrical arrangement of SPMs (508, 510, 530, 532) and confine concentrated plasma to one of an area 518 and an area 536 that is being operated for concentration of the plasma.

In an example, each detection unit comprises: a plurality of pairs of bifurcation channels (604, 606, 608, 610, 612, 614, . . . ), where each pair of bifurcation channels (606, 608) is to bifurcate plasma from a previous bifurcation channel (604) or from an inlet channel (602), through which plasma for detection of molecules is received, into two substantially equal plasma streams; at least one of a spectroscopy unit and a chemical reaction-based measurement unit installed in each bifurcation channel to determine a concentration of the molecules and/or the ions in the respective bifurcation channel; and a plurality of converging channels (632, 634, 636, 638, . . . ), where each converging channel is to combine two plasma streams from a pair of bifurcation channels or from two converging channels into a single stream.

In an example, the detection unit is to: determine whether the detected concentration of the molecules and/or the ions is less than or more than a predefined value; in response to detecting that the concentration is less than the predefined value, add a specific amount of the molecules and/or the ions to match the predefined value; and in response to detecting that the concentration is more than the predefined value, provide information to the correction unit about an amount of the molecules and/or the ions that are in excess, where the correction unit is to operate the channel (318, 320) to provide a specific amount to capturing molecules into one of the seventh cell (340) and eighth cell (342) to remove the excess amount of the molecules and/or the ions.

In an example, molecules and/or ions, equivalent to the molecules and/or the ions captured by the discarded capturing molecules, are added before infusing the plasma back to the subject.

In an example, the blood analysis system (360) comprises a control unit to cut-off or cause a flow of plasma and/or cellular component at each channel of the blood analysis system (360) via flow rate pumps.

LIST OF CITED REFERENCES

Ref1: Anal Chem. 2002 Aug. 1; 74(15): 420A-426A. The new wave of ion-selective electrodes. Ernö Pretsch.

Ref2: J Diabetes Sci Technol. 2008 September; 2(5): 882-889. Real-Time Continuous Glucose Monitoring in the Clinical Setting: The Good, the Bad, and the Practical. Irene Mamkin, Svetlana Ten Sonal Bhandari, Neesha Ramchandani.

Ref3: Pulse oximetry. Jubran A. Crit Care. 2015 Jul. 16; 19:272.

Ref4: Kraft J C, Osterhaus G L, Ortiz A N, Garris P A, Johnson M A (2009) In vivo dopamine release and uptake impairments in rats treated with 3-nitropropionic acid. Neuroscience 161(3):940-949.

Ref5: Zhang J, et al. (2013) In vivo monitoring of serotonin in the striatum of freely moving rats with one minute temporal resolution by online microdialysis-capillary high-performance liquid chromatography at elevated temperature and pressure. Anal Chem 85(20):9889-9897.

Ref6: Wassum K M, et al. (2012) Transient extracellular glutamate events in the basolateral amygdala track reward-seeking actions. J Neurosci 32(8):2734-2746.

Ref7: Sarter M, Kim Y (2015) Interpreting chemical neurotransmission in vivo: techniques, time scales, and theories. ACS Chem Neurosci 6(1):8-10.

Ref8: Couture M, Zhao S S, Masson J F (2013) Modern surface plasmon resonance for bioanalytics and biophysics. Phys Chem Chem Phys 15(27):11190-11216.

Ref9: Thompson M, Sheikh S, Blaszykowski C (2014) A perspective on the application of biosensor and lab-on-a-chip technologies to biomarker detection in biological fluids. Austin J Nanomed Nanotechnol 2(1):1009.

Ref10: Real-time measurement of small molecules directly in awake, ambulatory animals. Arroyo-Currás N, Somerson J, Vieira P A, Ploense K L, Kippin T E, Plaxco K W. Proc Natl Acad Sci USA. 2017 Jan. 24, 114(4):645-650

Ref11: Magnetic quantitative reverse transcription PCR: A high-throughput method for mRNA extraction and quantitative reverse transcription PCR Ricarda Jost, Oliver Berkowitz, and Josette Masle The Australian National University, Canberra, Australia BioTechniques 43:206-211 (August 2007) doi 10.2144/000112534

I claim:

1. A blood analysis system for analysis and correction of blood of a subject, the blood analysis system comprising:
a centrifugation unit to receive blood of a subject, the centrifugation unit is to:
hold capturing molecules, wherein one capturing molecule binds with, to chemically capture, one type of molecule or ion to render the bound molecule or the bound ion unfunctional; and
centrifuge to suspend cellular components with a minimal plasma along with the capturing molecules;
a holding unit coupled to the centrifugation unit to receive plasma with the capturing molecules but without the cellular components from the centrifugation unit and hold the received plasma;
an ion separation unit coupled to the holding unit to receive the plasma from the holding unit, the ion separation unit is to separate anions and cations from the received plasma based on electrostatically-charged semi permeable membranes; and
one or more filtration units to receive ion-free plasma with the capturing molecules expelled from the ion separation unit to filter out one or more specific types of molecules, not bound with the capturing molecules, from the ion-free plasma for detection and correction, before moving the ion-free plasma having the corrected filtered molecules towards a collecting channel for infusing back to the subject,
wherein the ion separation unit is coupled to the holding unit through a channel to receive the received plasma, and the ion separation unit comprises an anion separation unit and a cation separation unit, and
wherein the anion separation unit comprises:
a first cell coupled to the channel and having a first semi-permeable membrane of a specific molecular weight cut-off that allows the anions to pass through; and
a second cell coupled to the channel and having a second SPM, the second SPM being the same as the first SPM,
wherein one of the first cell and the second cell is operated to separate the anions and the other of the first cell and the second cell is operated for declogging,
wherein each of the first cell and the second cell is coupled to a respective concentration unit and a respective detection unit to concentrate and detect, respectively, the filtered anions, and
wherein the detection unit is coupled to a correction unit to correct a concentration of reconstituted anions expelled from the detection unit before passing the corrected anions towards the collecting channel.

2. The blood analysis system as claimed in claim 1, wherein the received plasma is diluted with water in the holding unit to control the viscosity of the received plasma.

3. The blood analysis system as claimed in claim 1, wherein the ion separation unit is to:
separate the anions before the cations, or
separate the cations before the anions.

4. The blood analysis system as claimed in claim 1, wherein the ion separation unit is to separate the anions and the cations from the received plasma with or without at least one of centrifugation and external electromagnetic field.

5. The blood analysis system as claimed in claim 1, wherein the cation separation unit comprises:
a third cell coupled to a channel to receive a retentate plasma from the first cell and the second cell and having a third semi-permeable membrane of a specific molecular weight cut-off that allows the cations to pass through; and
a fourth cell coupled to the channel to receive a retentate plasma from the first cell and the second cell and having a fourth SPM, the fourth SPM being the same as the third SPM,
wherein one of the third cell and the fourth cell is operated to separate the cations and the other of the third cell and the fourth cell is operated for declogging,
wherein each of the third cell and the fourth cell is coupled to a respective concentration unit and a respective detection unit to concentrate and detect, respectively, the filtered cations, and
wherein the detection unit is coupled to a correction unit to correct a concentration of reconstituted cations expelled from the detection unit before passing the corrected cations towards the collecting channel.

6. The blood analysis system as claimed in claim 5, wherein the first SPM, the second SPM, the third SPM, and the fourth SPM are negatively charged, when the anion separation unit is positioned before the cation separation unit in the ion separation unit.

7. The blood analysis system as claimed in claim 5, wherein the first SPM, the second SPM, the third SPM, and the fourth SPM are positively charged, when the cation separation unit is positioned before the anion separation unit in the ion separation unit.

8. The blood analysis system as claimed in claim 5, wherein each filtration unit comprises:
a fifth cell coupled to a channel to receive the ion-free plasma from the ion separation unit and having a fifth SPM of a specific molecular weight cut-off that allows molecules of a molecular weight equal to or less than the specific molecular weight cut-off to pass through; and
a sixth cell coupled to the channel to receive the ion-free plasma from the ion separation unit and having a sixth SPM, the sixth SPM being the same as the fifth SPM,
wherein one of the fifth cell and the sixth cell is operated to filter the molecules and the other of the fifth cell and the sixth cell is operated for declogging,
wherein chambers on both sides of the fifth and sixth SPMs of each of the fifth cell and the sixth cell are coupled to a respective concentration unit and a respective detection unit to concentrate and detect, respectively, the retentate and filtrate molecules,
wherein the detection unit, coupled to a retentate side of the fifth and sixth SPMs of the corresponding chamber, is coupled to a correction unit to correct a concentration of reconstituted molecules expelled from the detection unit before passing the corrected molecules towards the collecting channel, and
wherein the detection unit, coupled to a filtrate side of the fifth and sixth SPMs of the corresponding chamber, is coupled to a subsequent filtration unit for sequential filtration of molecules of a specific molecular weight less than the specific molecular weight cut-off associated with a previous filtration unit.

9. The blood analysis system as claimed in 8, wherein each of the correction units comprises:
a seventh cell coupled to a channel to receive plasma with the capturing molecules and with molecules and/or with ions that are to be corrected and having a seventh SPM of a specific molecular weight cut-off that allows molecules of a molecular weight equal to or less than the specific molecular weight cut-off to pass through; and
an eighth cell coupled to the channel to receive plasma with the capturing molecules and with molecules and/or or ions that are to be corrected and having an eighth SPM, the eighth SPM being the same as the seventh SPM,
wherein one of the seventh cell and the eighth cell is operated to separate the molecules and/or ions and/or the capturing molecules and the other of the seventh cell and the eighth cell is operated for declogging,
wherein the capturing molecules are removed from one of the seventh cell and eighth cell and discarded,
wherein chambers on a retentate side of the seventh and eighth SPMs of each of the seventh cell and the eighth cell:
are coupled to a channel to receive capturing molecules having a concentration depending on an amount of excess molecules and/or ions that are to be captured and removed from the plasma via the chambers on the retentate side, and
are coupled to a respective concentration unit and a respective detection unit to concentrate and detect, respectively, un-captured retentate molecules and/or ions during declogging of the seventh cell or the eighth cell or to correct a concentration of the un-captured retentate molecules and/or ions based on the detection,
wherein chambers on a filtrate side of the seventh and eighth SPMs of each of the seventh cell and the eighth cell are coupled to a respective concentration unit and a respective holding unit to concentrate and hold, respectively, filtrate molecules and/or ions before passing the filtrate molecules and/or ions towards the collecting channel.

10. The blood analysis system as claimed in claim 9, wherein each concentration unit comprises:
a ninth cell with a symmetrical arrangement of SPMs and a channel to receive plasma in a region between the symmetrical arrangement of SPMs;
a tenth cell with a symmetrical arrangement of SPMs and a channel to receive plasma in a region between the symmetrical arrangement of SPMs; and
an arrangement to allow water to circulate through the ninth cell and the tenth cell,
wherein one of the ninth cell and the tenth cell is operated to increase a concentration of the plasma and the other of the ninth cell and the tenth cell is operated for declogging,
wherein the water is circulated to create an osmotic pressure in the regions between the symmetrical arrangement of SPMs and confine concentrated plasma to one of an area of the ninth cell and an area of the tenth cell that is being operated for concentration of the plasma.

11. The blood analysis system as claimed in claim 9, wherein each detection unit comprises:
a plurality of pairs of bifurcation channels, wherein each pair of bifurcation channels is to bifurcate plasma from a previous bifurcation channel or from an inlet channel, through which plasma for detection of molecules is received, into two substantially equal plasma streams;
at least one of a spectroscopy unit and a chemical reaction-based measurement unit installed in each bifurcation channel to determine a concentration of the molecules and/or the ions in the respective bifurcation channel; and
a plurality of converging channels, wherein each converging channel is to combine two plasma streams from a pair of bifurcation channels or from two converging channels into a single stream.

12. The blood analysis system as claimed in claim 11, wherein the detection unit is to:
determine whether the detected concentration of the molecules and/or the ions is less than or more than a predefined value;
in response to detecting that the concentration is less than the predefined value, add a specific amount of the molecules and/or the ions to match the predefined value; and
in response to detecting that the concentration is more than the predefined value, provide information to the correction unit about an amount of the molecules and/or the ions that are in excess;

wherein the correction unit is to operate the channel to provide a specific amount to of the capturing molecules into one of the seventh cell and eighth cell to remove the excess amount of the molecules and/or the ions.

13. The blood analysis system as claimed in claim 9, wherein molecules and/or ions, equivalent to the molecules and/or the ions captured by the discarded capturing molecules, are added before infusing the plasma back to the subject.

14. The blood analysis system as claimed in claim 1, wherein the blood analysis system comprises:

a correction unit coupled to the centrifugation unit to receive the minimal plasma having the capturing molecules and the cellular components from the centrifugation unit, the correction unit is to extract the capturing molecules from the minimal plasma.

15. The blood analysis system as claimed in claim 14, wherein the minimal plasma having the cellular components is infused back to the subject along with replaced captured molecules and/or ions, and wherein the extracted capturing molecules are discarded.

16. The blood analysis system as claimed in claim 15, wherein the minimal plasma having the cellular components are suspended in an isotonic solution, and optionally with oxygen and glucose, before infusing back of the subject.

17. The blood analysis system as claimed in claim 1, wherein the blood analysis system comprises:

an SPM and/or a centrifuge to separate platelets from the minimal plasma;

a detection unit to receive the separate platelets and count the platelets; and a correction unit to correct the count of the platelets before infusing the minimal plasma with the corrected platelets to the subject.

18. The blood analysis system as claimed claim 17, wherein the minimal plasma, after separating the platelets, is ultra-centrifuged to separate granulocytes from the minimal plasma, and wherein the blood analysis system comprises:

a detection unit to count the granulocytes; and a correction unit to correct the count of the granulocytes, before infusing the minimal plasma with the corrected granulocytes to the subject.

19. The blood analysis system as claimed claim 17, wherein the minimal plasma, after separating the platelets, is ultra-centrifuged to separate red blood cells from the minimal plasma, and wherein the blood analysis system comprises:

a detection unit to count the RBCs; and a correction unit to correct the count of the RBCs, before infusing the minimal plasma with the corrected RBCs to the subject.

20. The blood analysis system as claimed in claim 1, wherein the blood analysis system comprises a control unit to cut-off or cause a flow of plasma and/or cellular component at each channel of the blood analysis system via flow rate pumps.

* * * * *